US 11,533,855 B2

(12) United States Patent
Davis et al.

(10) Patent No.: US 11,533,855 B2
(45) Date of Patent: Dec. 27, 2022

(54) PROCESS AND APPARATUS FOR PROVIDING DURABLE PLANT TAGS FOR HORTICULTURAL ORGANIZATION

(71) Applicant: Orora Visual TX LLC, Mesquite, TX (US)

(72) Inventors: Jack Davis, Dallas, TX (US); Andrew Levi, Dallas, TX (US)

(73) Assignee: Orora Visual TX LLC, Mesquite, TX (US)

(*) Notice: Subject to any disclaimer, the term of this patent is extended or adjusted under 35 U.S.C. 154(b) by 433 days.

(21) Appl. No.: 15/230,015

(22) Filed: Aug. 5, 2016

(65) Prior Publication Data

US 2018/0035614 A1    Feb. 8, 2018

(51) Int. Cl.
| | | |
|---|---|---|
| A01G 2/00 | (2018.01) | |
| A01G 22/00 | (2018.01) | |
| G01N 33/00 | (2006.01) | |
| A01G 9/00 | (2018.01) | |

(52) U.S. Cl.
CPC .............. *A01G 2/00* (2018.02); *A01G 22/00* (2018.02); *G01N 33/0098* (2013.01); *A01G 9/006* (2013.01)

(58) Field of Classification Search
CPC .......... A01G 2/00; A01G 22/00; A01G 9/006; G01N 33/0098
USPC ............................................................. 702/2
See application file for complete search history.

(56) References Cited

U.S. PATENT DOCUMENTS

| | | |
|---|---|---|
| 4,570,368 A | 2/1986 | Stover |
| 4,791,742 A | 12/1988 | Stover |
| 4,972,616 A | 11/1990 | Doll |
| 5,575,107 A | 11/1996 | Doerr |
| 5,941,019 A | 8/1999 | Guarriello et al. |
| 6,164,537 A | 12/2000 | Mariani et al. |
| 7,438,224 B1 | 10/2008 | Jensen et al. |
| 7,702,462 B2 | 4/2010 | Fuessley et al. |
| 7,761,334 B2 | 7/2010 | Pickett et al. |
| 8,205,789 B2 | 6/2012 | Mori |
| 8,258,951 B2 | 9/2012 | Hyde et al. |
| 8,279,066 B2 | 10/2012 | Hyde et al. |
| 8,301,389 B2 | 10/2012 | Dunlap |
| 8,373,563 B2 | 2/2013 | Hyde et al. |
| 8,577,616 B2 | 11/2013 | Dunlap |

(Continued)

FOREIGN PATENT DOCUMENTS

| | | |
|---|---|---|
| CA | 2809253 | 9/2014 |
| EP | 1433377 B1 | 3/2008 |

(Continued)

OTHER PUBLICATIONS

NPL_015_1 Search Results, Jul. 11, 2021, 1 pp. (year: 2021).*

(Continued)

*Primary Examiner* — Toan M Le
*Assistant Examiner* — Xiuqin Sun
(74) *Attorney, Agent, or Firm* — Martin & Ferraro, LLP

(57) ABSTRACT

A system and method for selecting plants based on climate data and plant data. The system receives climate data and plant data and selects plants for a geographical division based on the climate data and plant data. The system generates durable plant tags with for the plants that have an icon that identifies the lighting level and watering level of the plants using a color and a number.

9 Claims, 16 Drawing Sheets

(56) References Cited

U.S. PATENT DOCUMENTS

| | | |
|---|---|---|
| 8,670,940 B2 | 3/2014 | Hirose et al. |
| 8,800,860 B2 | 8/2014 | Van et al. |
| 2004/0237368 A1 | 12/2004 | Paskesen et al. |
| 2005/0132305 A1 | 6/2005 | Guichard et al. |
| 2005/0144027 A1 | 6/2005 | Brunner et al. |
| 2005/0172530 A1 | 8/2005 | Huffman |
| 2006/0272208 A1 | 12/2006 | Altman et al. |
| 2007/0079536 A1 | 4/2007 | Hall |
| 2008/0220529 A1 | 9/2008 | Hulme |
| 2009/0243832 A1 | 10/2009 | Hyde |
| 2011/0120902 A1 | 5/2011 | Boswell |
| 2011/0264559 A1 | 10/2011 | Barrientos et al. |
| 2011/0289832 A1 | 12/2011 | Kelly |
| 2012/0010789 A1 | 1/2012 | Dulnigg |
| 2012/0098641 A1 | 4/2012 | Whittle |
| 2012/0191817 A1 * | 7/2012 | Sayan ............. G06Q 30/0601 709/219 |
| 2012/0323911 A1 | 12/2012 | Anton et al. |
| 2013/0180138 A1 | 7/2013 | Luea |
| 2014/0149236 A1 | 5/2014 | Argue |
| 2014/0168412 A1 * | 6/2014 | Shulman ............. H04N 7/18 348/89 |
| 2015/0052028 A1 | 2/2015 | Wooden et al. |
| 2015/0081058 A1 * | 3/2015 | Oliver ................. A63F 13/245 700/91 |
| 2015/0096080 A1 | 4/2015 | Davies et al. |
| 2017/0270323 A1 | 9/2017 | Butler |
| 2020/0154644 A1 * | 5/2020 | Cox ................... A01G 9/0293 |

FOREIGN PATENT DOCUMENTS

| | | | |
|---|---|---|---|
| WO | 0109711 | 2/2001 | |
| WO | 2004060746 A2 | 7/2004 | |
| WO | 2006102246 | 9/2006 | |
| WO | 2015192066 | 12/2015 | |
| WO | WO-2015192066 A1 * | 12/2015 | ......... G06K 7/10366 |

OTHER PUBLICATIONS

NPL_015_2 Search Results, Jul. 11, 2021, 1 pp. (year: 2021).*

Elmorshidy, A., "Radio Frequency Identifiers: What are the Possibilities?" Journal of Telecommunications, vol. 2, Issue 2, (May 2010), pp. 21-24.

Garber, M.P., et al., "Selling Plants through Horticultural Distribution Centers," Journal of Environmental Horticulture vol. 18, Issue 3, (Sep. 2000), pp. 179-183.

Jupe, M.K., et al., "The Impact of Information Technology on Green Industry Marketing," Proceedings of Southern Nurserymen's Association Research Conference: Forty-Seventh Annual Report, vol. 47. (no month, 2002), pp. 511-578.

Molla, A., et al., "E-Business Diffusion in Australia's Horticulture Supply Chain," RMIT University School of Business Information Technology (May 2008), 12 pages.

Reid, N., et al., "Importin Change: Canadian Competition and the U.S Floriculture Industry," The Industrial Geographer vol. 6, Issue 1, (no month, 2009): pp. 3-19.

Google Scholar search "temperature" "sunlight" "light intensity" "exponential decay" "growth" in Office Action dated Feb. 12, 2021 for co-pending U.S. Appl. No. 16/436,584.

Google Scholar search "light intensity" "exponential decay" "constant" in Office Action dated Feb. 12, 2021 for co-pending U.S. Appl. No. 16/436,584.

Google Scholar search "soil temperature" "light intensity" "exponential decay" in Office Action dated Feb. 12, 2021 for co-pending U.S. Appl. No. 16/436,584.

* cited by examiner

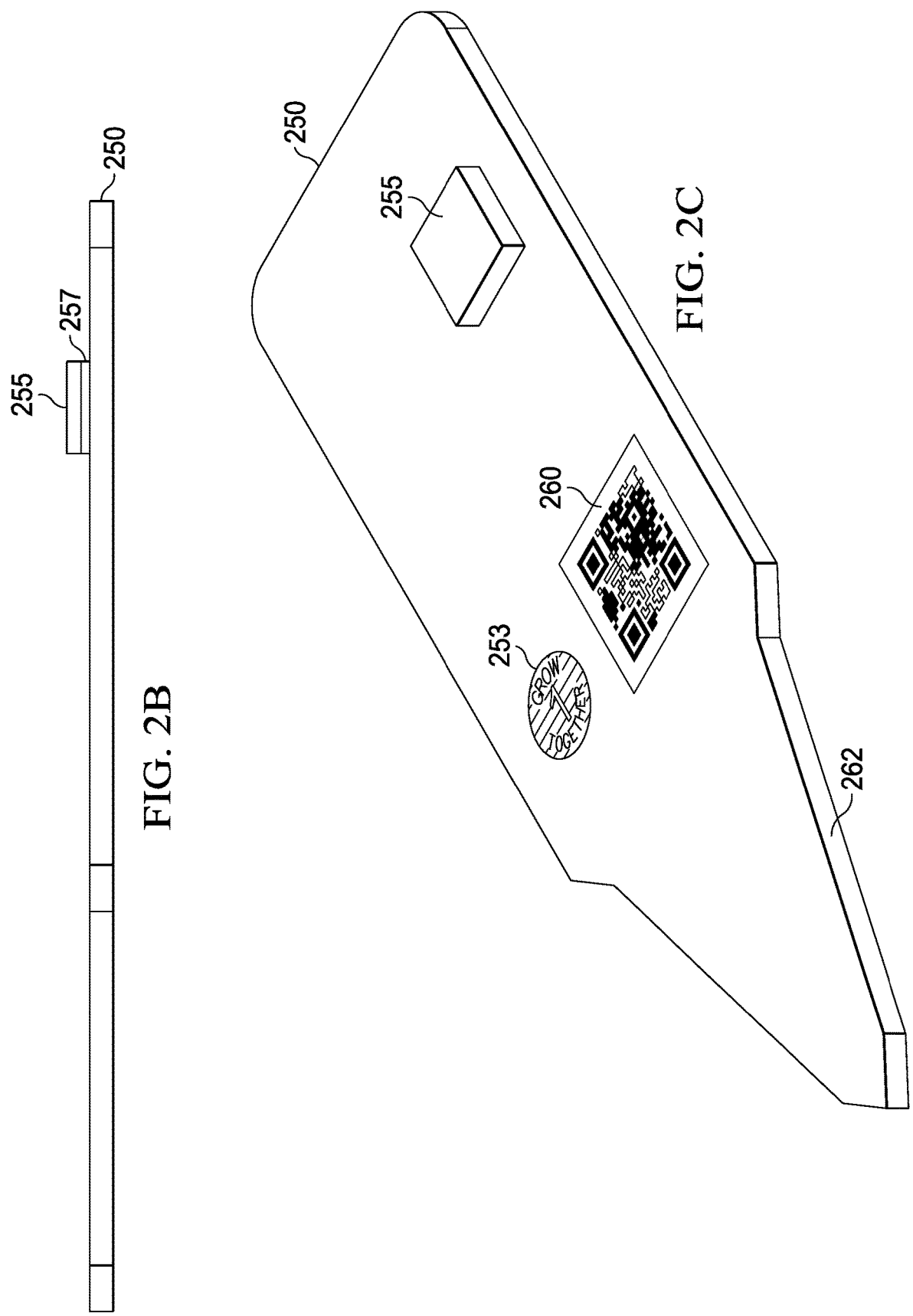

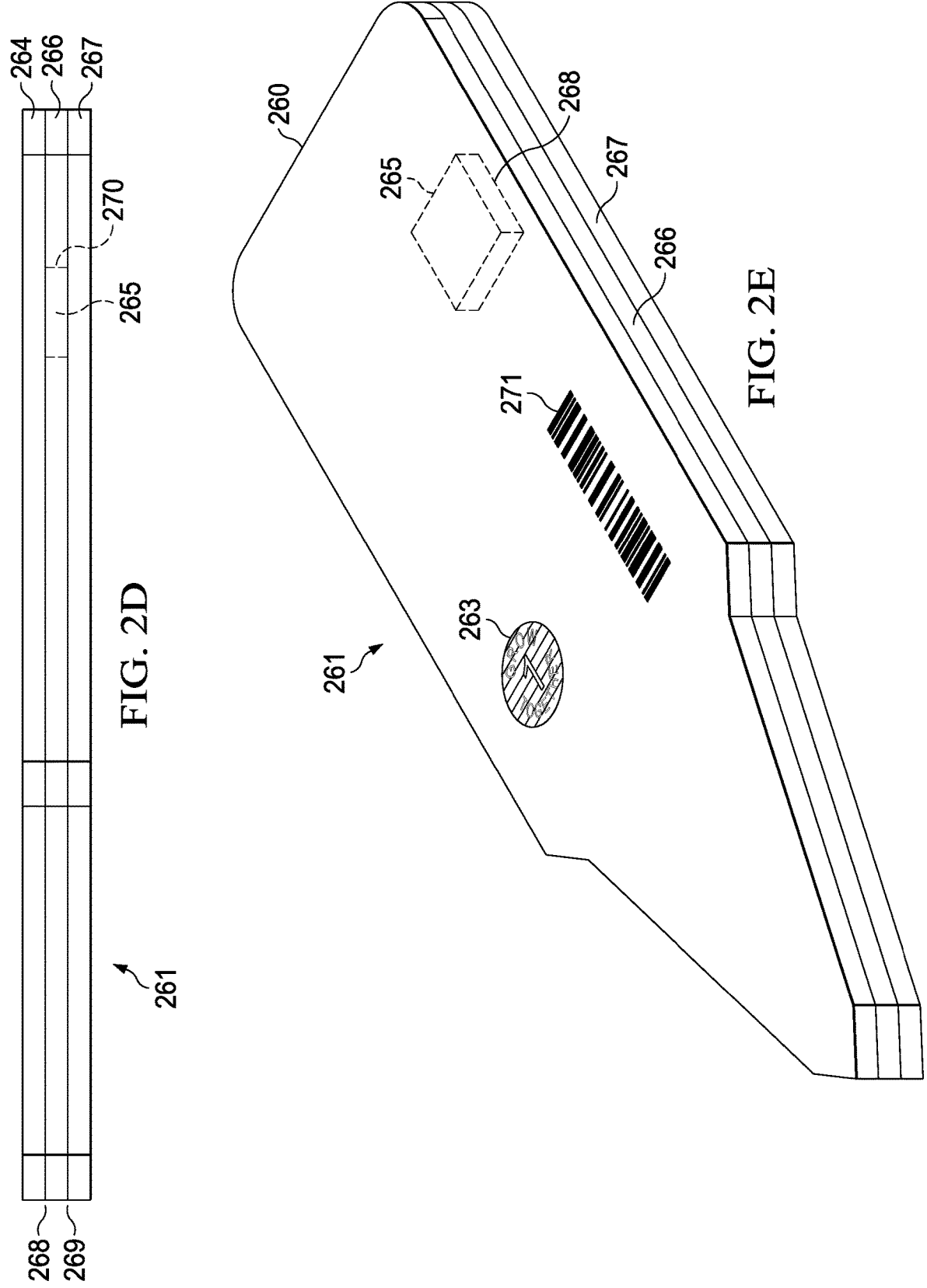

PROCESS AND APPARATUS FOR PROVIDING DURABLE PLANT TAGS FOR HORTICULTURAL ORGANIZATION

FIELD

The present invention relates to systems for delivering horticultural data for gardening and landscaping. More particularly, the invention relates to a system that identifies plants that grow well together in a specific location and provides continually updated horticultural information based on local climate data and specific plant characteristics through an active programmable electronic plant tag and data delivery system.

BACKGROUND

Gardeners and landscapers often struggle to identify and select plants that will coexist in a landscape setting. Each landscape setting is different, offering differing amounts of water and shade in different spots. Extensive horticultural information and experience is often required to choose different plants that grow well together and avoid expensive trial and error in selecting various plants to complete a functional landscape.

The problems of choosing plants for a landscape is complicated by the fact that different geographic regions have different climate and soil types. Temperature, light, and precipitation all differ from region to region. Similarly, different geographic regions have different pH levels in local soil. Because of this, plants grow differently and require different maintenance and fertilization depending on the geographic region in which they are planted.

Further complicating the task of gardening and landscaping is the fact that climate is dynamic. That is, the climate is changing. In order to choose plants that will do well over an extended period of time it is necessary to have updated climate data on a regular basis and to change plant care to coincide with changing climatic conditions.

Data and information describing climate types, soil and plant characteristics is available. For example, the National Oceanic and Atmospheric Administration provides temperature and precipitation data for various districts of the United States. However, the data is not available on a highly localized basis, but rather for wide geographic areas. The data also is not available in a way that is closely associated with various plant types. Further, while the data is available, it is not easy to use.

The prior art has failed to provide a way to centralize, update, and summarize climatic information. Further, the prior art has failed to provide a way to deliver that information in a way close to a plant so that it may be easily used to initially choose plants for a landscape or garden and then later to care for and fertilize them.

Therefore, there is a need for a system and method that provides correct and up to date horticultural information for different plants that is specific to different geographical regions to aid in choosing plants for a landscape and maintaining them. There is also a need for a way to deliver the information in close proximity to the plants so that it can be updated and used over a long period of time.

BRIEF DESCRIPTION OF THE DRAWINGS

The disclosed embodiments will be described with reference to the accompanying drawings.

FIG. 2b-2c shows a preferred embodiment of a durable plant tag, including an NFC chip.

FIG. 2d-2e shows a preferred embodiment of a durable plant tag, including a hermetically sealed NFC tag.

FIG. 6b-1 is a data flow diagram of the print GPS specific tag function in an alternate embodiment in accordance with the disclosure.

FIG. 6b-2 is a data flow diagram of the print GPS specific tag function in an alternate embodiment in accordance with the disclosure.

DETAILED DESCRIPTION

Figure 1:
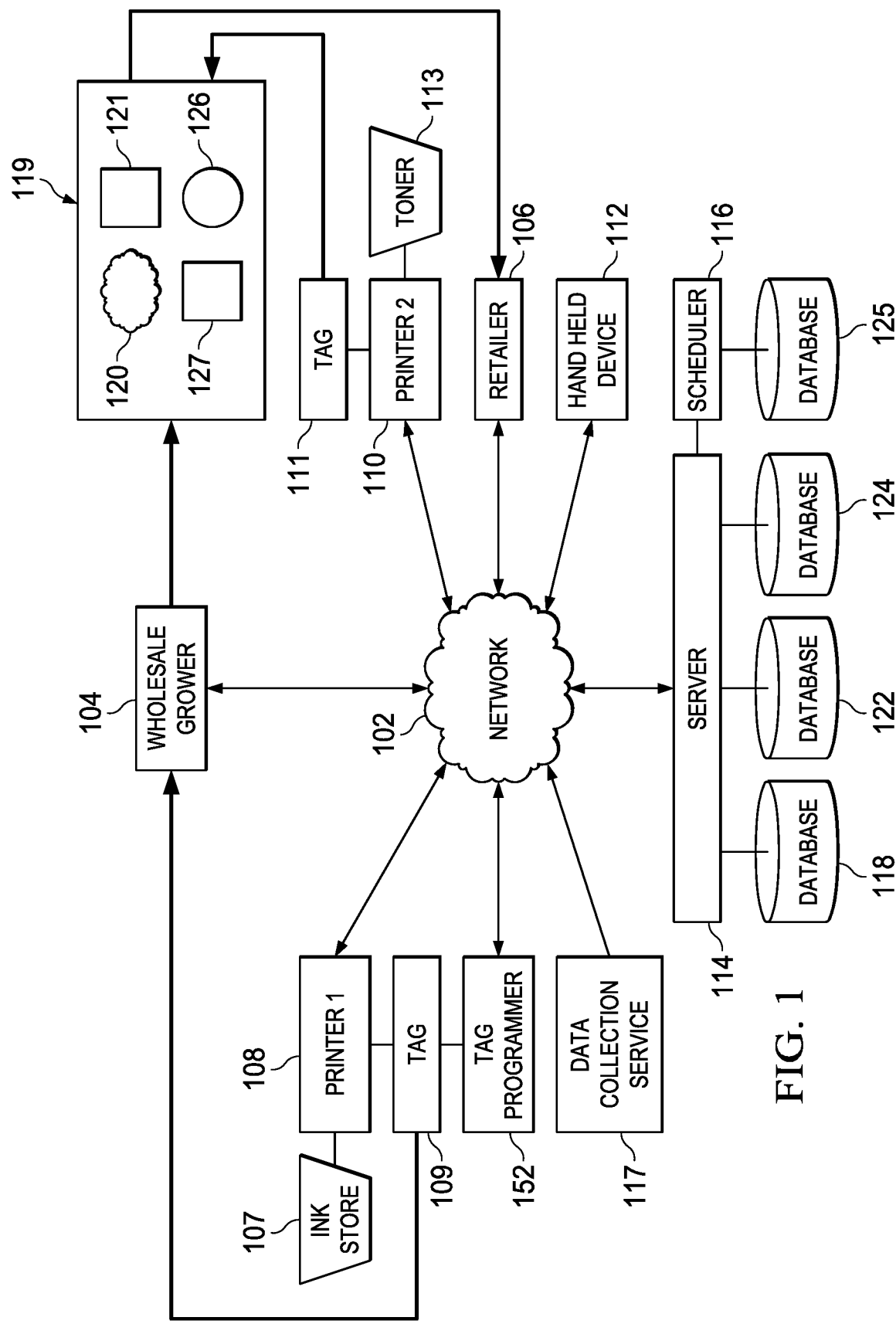
FIG. 1 is a system architecture diagram in accordance with one embodiment of the disclosure.

FIG. 1 is a system architecture diagram in accordance with one embodiment of the disclosure. Network 102 is a computer network, such as the Internet, which allows computers and electronic devices to exchange data over one or more wired or wireless data links. Network 102 interconnects and allows for communication of data and information between one or more devices, such as server 114, data collection service 117, first printer 108, second printer 110, wholesale grower 104, retailer 106, hand held device 112, scheduler 116 and databases 118, 122, 124 and 125.

Each of the devices may include computer programs that are resident in memory and which control the functions of the devices. The computer programs may also be resident on fixed media, such as a hard drive or optical disk. The computer programs may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages.

In one embodiment, communication of data takes place over the Internet using one or more communication protocols, including: Transmission Control Protocol (TCP)/Internet Protocol (IP), Hypertext Transfer Protocol (HTTP), HTTP Secure (HTTPS).

Wholesale grower 104 can be any provider of plants that include: green plants, flowering plants, seed plants, vegetables, trees, and so on, that are arranged for care and displayed at retailer 106 and which generally require certain levels of light and moisture for growth. In one embodiment, wholesale grower 104 is a typical greenhouse that grows plants in regulated climatic conditions. Wholesale grower 104 may also include a plant nursery or a large scale plant manufacturer. Wholesale grower 104 includes screening installations and equipment for heating, cooling, and lighting to control and optimize the conditions for plant growth. In a preferred embodiment wholesale grower 104 also includes second printer 110 that in combination with software and special tag substrates and inks, is capable of printing durable plant tag 111.

Data collection service 117 is connected to the network and communicates through the network to server 114. In one embodiment, the data collection service provides information related to temperature, precipitation and soil pH for each geographic location in the United States as defined by a set of GPS coordinates. The information is extrapolated for each location by a spline function from known empirical data supplied for each division of the country. In one embodiment, this extrapolated data is available from Climate Source Corporation of Austin, Tex. In another embodiment, this extrapolated information is available from empirical data supplied by the National Oceanic and Atmospheric Administration of the United States (NOAA).

Retailer 106 can be any facility that provides for display of plants from wholesale grower 104. In one embodiment, retailer 106 is a retail outlet that receives plants from wholesale grower 104 and displays them to one or more users that each have a hand held device 112. Retailer 106 communicates with server 114 and processes data and information related to the plants that are made available and/or are on display.

Hand held device 112, in typical embodiments, is a smart phone, laptop computer, or PC workstation. The hand held device can be wireless or hard-wired to the network. Hand held device 112 connects to server 114 to aid the user in selecting, organizing and maintaining plants. Through the use of an app, a web browser, or the like, hand held device 112 connects to server 114 via network 102. Hand held device 112 receives data and information from the user and communicates this data and information to server 114. Hand held device 112 also displays data, information, and media that is received from server 114. Hand held device 112 includes the hardware and software necessary to receive and process the signal provided by NFC tags as will be further described.

Server 114 is connected to network 102 and receives, processes, and transmits data and information related to the plants and plant tags. Server 114 is connected to databases 118, 122, and 124, which are used to store and manage data and information. Server 114 communicates with data collection service 117 via network 102 to receive data and information pertinent to retailer 106, including data, information, and media related to plants that are displayed at retailer 106. Server 114 communicates with hand held device 112 via network 102. In one embodiment, server 114 is located at a data center that is separate from retailer 106.

Scheduler 116 is connected to network 102. The scheduler receives, processes, and transmits data and information related to calculation of, logging and scheduling of electronic alerts that are sent from server 114 to hand held device 112 through network 102. Scheduler 116 is connected to database 125, which is used to store and manage data and information related the alerts.

First printer 108 and second printer 110 print information on a durable substrate that becomes the durable plant tags. First printer 108 can be located at retailer 106, wholesale grower 104, or at another location. In one embodiment, the substrate is a rolled stock. The rolled stock is pre-perforated in the final tag shape. In another embodiment, the printers print onto a flat press layout. A press layout contains multiple tags depending on the size of the press sheet running through the press. Printing plates for UV Sheet-fed, flexographic, and letterpress are made from the press layout. The plates are necessary for the printing process. After printing (two sides) the press sheet is die cut. The tags are die cut into the shape pre-determined by the design. After die cutting is complete the tags remain in the press sheet. In either case, the tags are then removed, sheets packaged, boxed, and shipped to the wholesale grower.

In another embodiment, a press layout file is sent to a digital press. Depending on the type of plant tag and quantity of tags ordered either pre-die cut or non-die-cut sheets of stock can be printed.

In another embodiment, an encrypted file is supplied for use in printing tags using a laser printer and pre-die cut stock. The encrypted file is decrypted by the system and sent to the printer. The encryption prevents changing the file or using it for other purposes.

In a preferred embodiment second printer 110 is an 931C printer available from Oki USA Corporation. Second printer 110 includes polymer based toner 113. In a preferred embodiment toner 113 comprises a multi-color toner; cyan, yellow, black and magenta. The formulations of the toner used to print the tags are adapted to withstand very long term exposure to UV radiation and widespread temperature variation so as to semi-permanently adhere to the substrate and not fade so as to mark the plant for further identification and maintenance. In one embodiment, the toner includes part numbers Cyan—45536515; Magenta—45536514; Yellow—45536513; Black—45536516 available from Oki USA Corporation.

In a preferred embodiment first printer 108 is an UV sheetfed letter press or Flexo Press printer available from Oki USA Corporation. First printer 108 includes internal ink store 107. In a preferred embodiment ink store 107 comprises a multi-color UV printing ink. The formulations of the inks used to print the tags are adapted to withstand very long term exposure to UV radiation and widespread temperature variation so as to semi-permanently mark the plant for further identification and maintenance. In one embodiment, the ink store includes light resistant ink available from Oki USA Corporation.

In a preferred embodiment, the UV sheetfed printer may be any of the following: KBA Rapida 205/81"; Mitsubishi+coater/40"; Mitsubishi+coater/41"; KBA Genius 52UV. The flexographic printer may be any of the following: Mark Andy 4150 Rotary Press; Mark Andy 4200 Rotary Press; Rotopress 13"; Rotopress 10". And, the rotary letter press may be any of the following: 3-Sanki UV Letterpress.

Tag programmer 152 is connected to network 102 and communicates with server 114 through that network. Each NFC tag 127 travels through tag programmer 152. Tag programmer 152 encodes the NFC tag with a unique number as will be further described. The values and data that are to be written to each NFC tag 127 are stored in a database that is accessed by NFC encoder software. The NFC encoder software controls tag programmer 152 to create a wireless data connection to each NFC tag 127 as it passes over the NFC reader and copy the information from one row of the database into one NFC tag 127. The NFC encoder software then tests NFC tag 127 to verify that the information was properly sent. In a preferred embodiment, tag programmer 152 comprises an ACR122U USB NFC Reader from Advanced Card Systems (ACS) that is configured for high speed reel-to-reel encoding of NFC tags 127. NFC encoder software, such as that from GoToTags, controls tag programmer 152 to program NFC tags 127.

After the plants have sufficiently grown, the tags are durably attached to the plants or plant containers and are shipped to retailer 106 to be displayed.

In a preferred embodiment, durable plant tag 119 includes image 120, barcode 121, icon 126 and NFC tag 127. In another embodiment, the durable plant tag does not include the NFC tag. Image 120 includes a picture of the mature plant and text, data and horticultural information related to the plant. The text, data and horticultural information can be generalized to be applicable for any geographic region, or alternatively, they can be specialized for each type of plant and each geographic location where the plant will be located. Icon 126 is a novel symbol, determined by server 114, that summarizes certain horticultural characteristics of the plant that are specific to GPS location and plant type.

The substrate of the tags of a preferred embodiment is a styrene, polypropylene or polyethylene, as will be further described. Each tag is comprised of a durable plastic formulation which includes UV stabilizers to protect it from degradation due to long term exposure to ultraviolet radiation. In the preferred embodiment, the UV stabilizer is a benzophenone in a concentration range from about 0.05% to about 4%. In another embodiment, the UV stabilizer is a triazole in a concentration from about 0.05% to about 4%.

NFC tag 127 is uniquely programmed to respond to a near field communications signal with data that uniquely identifies the type of plant or the plant ID. In another embodiment, the plant ID and the GPS location where the plant will be located when mature are combined into a unique number with a hash function. In a preferred embodiment, the hash function is a simple check sum. In a preferred embodiment, the NFC tag is an NXP integrated circuit model number DESFIRE EV1 and operates at 13.56 MHz. It is capable of reading and writing 8 k bytes of information and is compliant with 150 144438A protocol. In a preferred embodiment, the NFC tag is also ISO 1800-3 and ISO 13157 compliant.

Figure 2A:
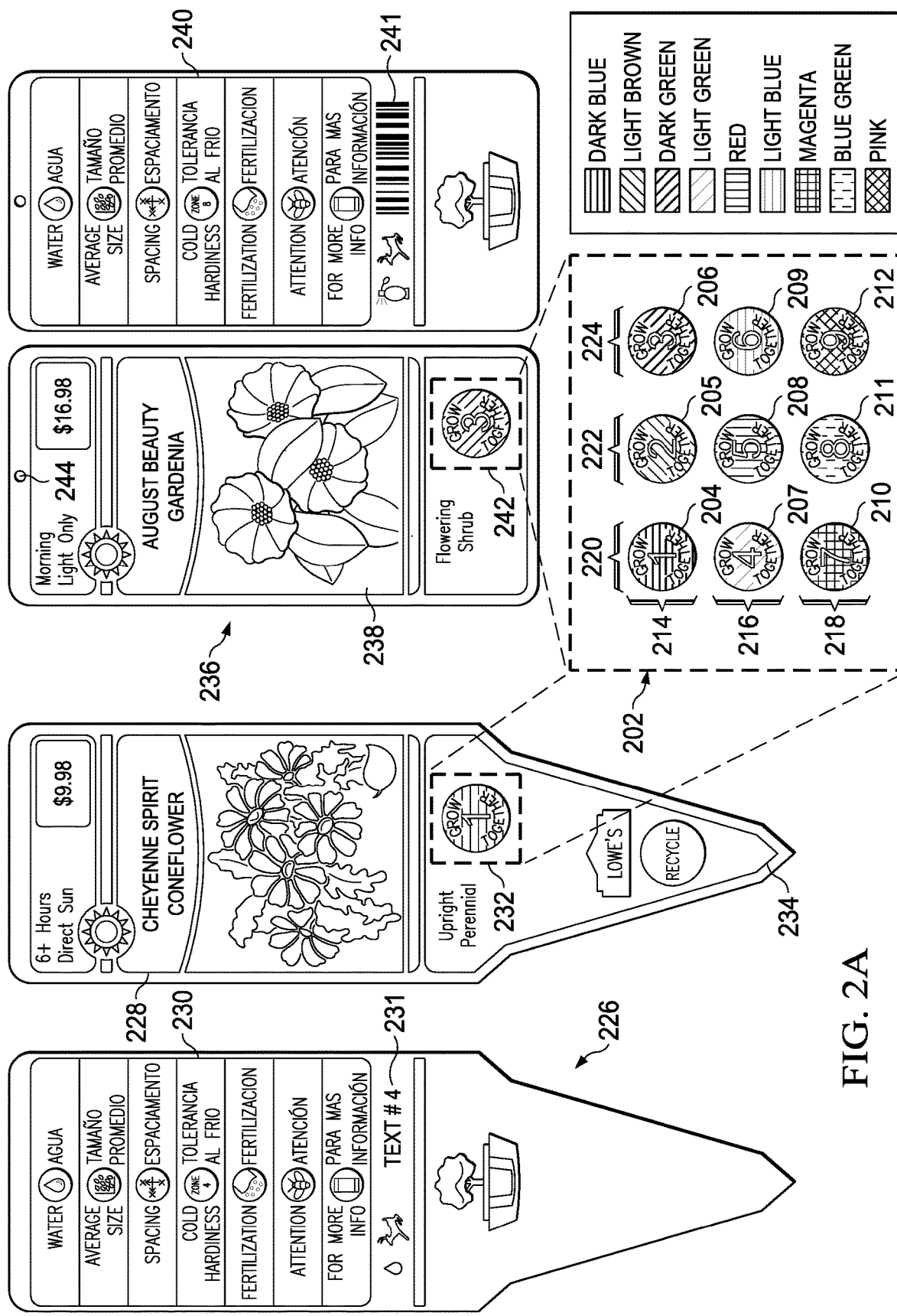
FIG. 2a shows a durable plant tag, constructed according to a preferred embodiment.

FIG. 2A shows two preferred embodiments of durable plant tags 109 and 111 including group of exemplary icons 202.

Group of icons 202 includes icons 204 to 212 that include a plant guide number and color. Each plant guide number is encoded with a "light value" and a "watering value" as indicated in Table 1 below. The plant guide numbers are used to summarize GPS specific horticultural data for each plant type. The same colors are used consistently to represent the same plant guide numbers so as to increase ease of recognition by the consumer. In an alternate embodiment, different shapes may be substituted for different colors, or used in conjunction with the colors, so long as they are consistent for each plant guide number. Plants that bear durable plant tags having the same icon color and plant guide number require similar light levels and watering levels and will grow successfully in the same geographic regions.

TABLE 1

| Icon | Tag Number | Tag Color | Watering Level | Light Level |
| --- | --- | --- | --- | --- |
| Icon 204 | 1 | Dark blue | Low | High |
| Icon 205 | 2 | Light brown | High | High |
| Icon 206 | 3 | Dark green | Medium | High |
| Icon 207 | 4 | Light green | Low | Medium |
| Icon 208 | 5 | Red | High | Medium |
| Icon 209 | 6 | Light blue | Medium | Medium |
| Icon 210 | 7 | Magenta | Low | Low |
| Icon 211 | 8 | Blue green | High | Low |
| Icon 212 | 9 | Pink | Medium | Low |

The coding in Table 1 is for one embodiment and a different coding and color schemes may be used in other embodiments.

Group of icons 202, including icons 204-212, are coded to three different watering levels: low watering level 220, high watering level 222, and medium watering level 224. Group of icons 202 are also coded to three different light levels: high light level 214, medium light level 216, and low light level 218. In a preferred embodiment, a "high" light level means full sun; a "medium" light level means part sun; and a "low" light level means shade. Using group of icons 202 on adjustable plant tag allows for more accurate placement and maintenance of plants by the user without extensive horticultural knowledge. Group of icons 202 in long term attachment to the plant also promotes more accurate care and watering of the plant due to the long term availability of the tag in close proximity to the plant.

Durable plant tag 226 includes a first side 228, a second side 230 and icon 232. Durable plant tag 226 is constructed of styrene or polystyrene plastic approximately 8 mils thick. A UV inhibitor is introduced into the plastic composition to increase stability in sunlight and to increase the durability of the tag. In a preferred embodiment, a phenolic antioxidant and phosphate is added to the plastic composition such as loxinox GP45 or Weston TNPP. First side 228 and a second side 230 include data and information that is human readable and relates to the plant. In one embodiment, durable plant tag 226 includes a unique number 231 which is used to retrieve information about the plant via a short message service text message, as will be further described. In one preferred embodiment, durable plant tag 226 includes spike 234 that allows it to be inserted in the soil.

In another embodiment, durable plant tag 236 includes first side 238, second side 240, and icon 242. Durable plant tag 236 includes hole 244 that allows durable plant tag 236 to be permanently attached to the plant by a sturdy cord (not shown).

Icon 232 is an embodiment of icon 204 and, indicates that the plant needs a low level of water and a high level of light. Icon 242 is an embodiment of icon 206 and indicates that the plant needs a medium level of water and a high level of light. The plant packaged with durable plant tag 226 has similar light requirements to the plant packaged with durable plant tag 236, both needing a high level of light. However, the plant packaged with durable plant tag 226 has different water requirements from the plant packaged with durable plant tag 236, the plant with durable plant tag 226 needs a low level of water and the plant with durable plant tag 236 needs a medium level of water.

In another embodiment, barcode 241, such as a quick response (QR) code, is included on the durable tag. In this embodiment, the barcode is resolved by the application running on the hand held device to a website address that allows hand held device 112 to access a website on a server, such as server 114, as will be further described.

Referring then to FIGS. 2b-2c, are other preferred embodiments of durable plant tag 119 are described.

Durable plant tag 250 is comprised of a plastic substrate as previously described. NFC tag 255 is durably fixed to durable plant tag 250 with adhesive layer 257. An epoxy resin is preferred. Other durable adhesives can be employed with equal success. Affixed to a front surface of durable plant tag 250, is icon 253, as previously described, and QR code 260. In this preferred embodiment, durable plant tag 250 includes plant stake 262.

Referring then to FIGS. 2d-2e, are other preferred embodiments of a durable plant tag is described. Durable plant tag 261 is comprised of the three layers 264, 266, 267. Layer 264 is joined to layer 266 by adhesive layer 268. Layer 266 is joined to layer 267 by adhesive layer 269. Suitable adhesives are UV resistant. An epoxy resin is preferred. Heat welding may be substituted for adhesive bonding. Each of the layers is a durable plastic substrate as previously described. In this embodiment, each layer is approximately 3 Mils thick but can useful within the range between about 2 Mils and about 8 Mils a piece. NFC tag 265 is hermetically sealed between layers 264 and 267, in void 270. As such, NFC tag 265 is protected from the elements which adds to the durability of the tag system.

In one preferred embodiment, a front face of durable plant tag 261 includes icon 263 and barcode 271. Barcode 271 and NFC tag 265 are encoded with a unique identifying number as will be further described.

FIGS. 3a-3e are data structure diagrams for data and information used in accordance with one embodiment of the system used to provide the durable plant tag. The data structures indicate groupings of related types of data in relational database such as databases 118, 122 and 124 that are in communication with server 114 and database 125 that is in communication with scheduler 116.

Figure 3A:
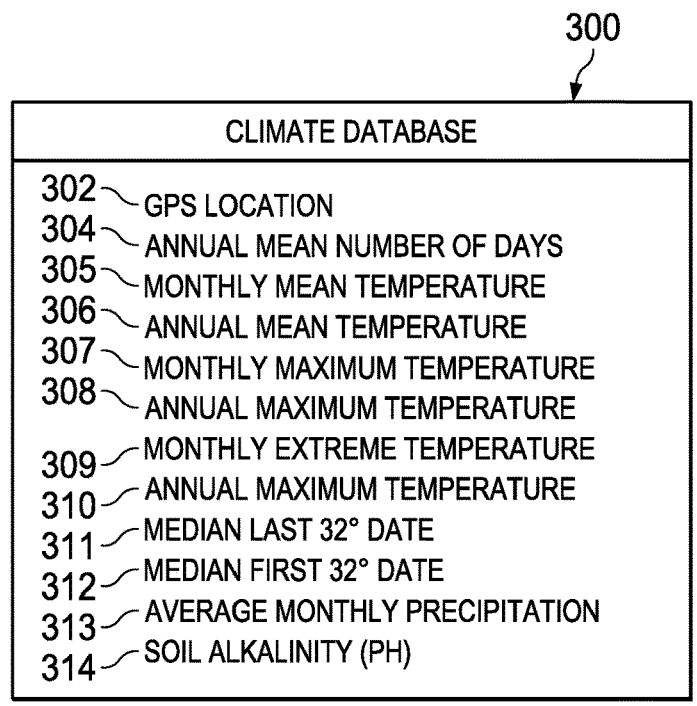
FIG. 3a shows a climate database diagram in accordance with an embodiment of the disclosure.

In FIG. 3a, climate database 300 includes a record for each GPS location 302 in the United States. For each GPS location 302, the database includes an entry for annual mean number of days 304 that the maximum temperature is greater than 90 degrees, monthly mean temperature 305, annual mean temperature 306, monthly maximum temperature 307, annual maximum temperature 308, mean extreme monthly temperature 309, and annual maximum temperature 310. Also for each GPS location the climate database includes entries for median date of the last 32 degree Fahrenheit temperature day in the spring 311 and median date of the first 32 degree Fahrenheit temperature day in the fall 312. These dates are considered the "last freeze date" and "first freeze date", respectively. Climate database 300 also includes an entry for each GPS location in the United States for average monthly precipitation 313. Climate database 300 also includes an entry for soil alkalinity 314 for each GPS location in the United States.

Figure 3B:
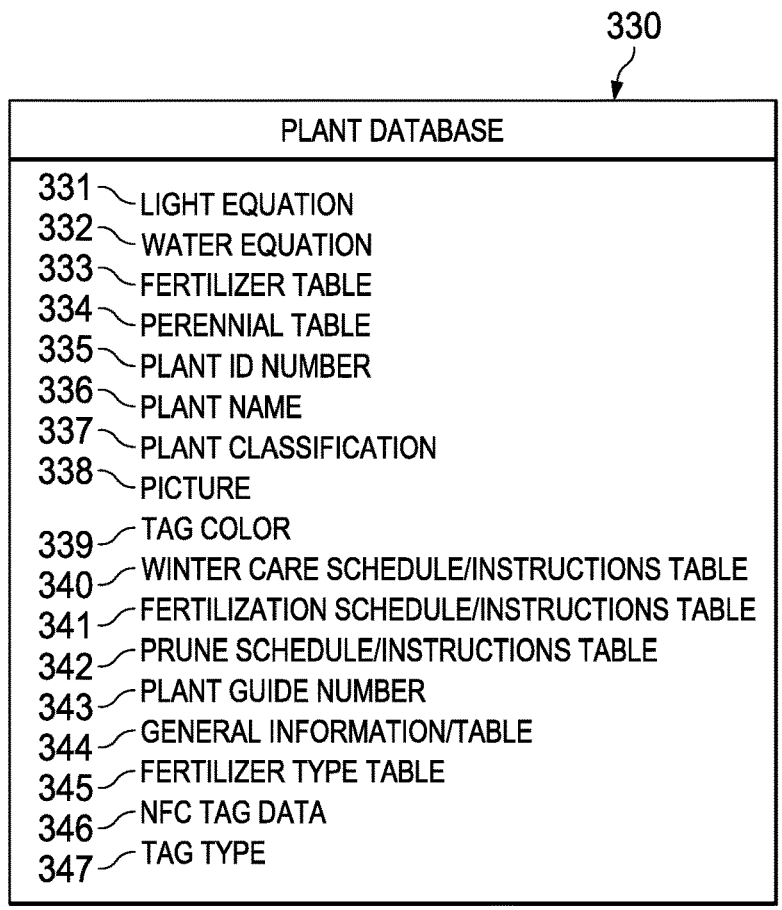
FIG. 3b shows a plant database diagram in accordance with an embodiment of the disclosure.

Referring then to FIG. 3b, plant database 330 includes a record for each plant type. Plant database 330 includes a light equation 331, a water equation 332 and a fertilizer table 333, as will be further described. Plant database 330 includes a perennial table 334. Plant database 330 can include a pre-calculated plant guide number 343. Plant database 330 can also include a tag type 347 to identify the physical make up and construction of the tag that is most durable for that type of plant.

Plant ID number 335 uniquely identifies a type of plant. Plant name 336 includes text that identify a common name of the plant.

Plant classification 337 includes the scientific name of the plant, including the kingdom, subkingdom, superdivision, division, class, subclass, order, family, genus, species, subspecies, and variety of the plant.

Picture 338 includes a data field for one or more images the plant when fully grown. In an alternative embodiment, plant database 330 includes additional forms of media, such as video, mp4, audio, mp3 and graphic and three dimensional models for the plant.

Plant guide number 343 is a numerical value that is indicative of plant light and watering requirements, as shown in Table 1 above.

Tag color 339 is a specific color that is indicative of plant maintenance requirements, as shown in Table 1 above. In a preferred embodiment, the shape of the icon is also stored in this field.

General information 344 is a text field that contains general information about the plant such dimensions, planting instructions and care instructions. In one preferred embodiment, general information 344 includes a table that associates a set of GPS coordinates for an area to specific general information for each type of plant when planted in that area. The table is stored as a set of GPS coordinates associated with a general information text field stored in each plant record for each plant ID in a plant database. An example of the general information table is shown in Table 2 below.

TABLE 2

| GPS Coordinates | General Information |
|---|---|
| 32.77°N, 96.79°W | Plant requires shade in the summer |
| ... | ... |
| 41.87°N, 87.62°W | Avoid exposing plant to insects in the summer |

Winter care schedule instructions table 340 includes a table having a text field in which is stored instructions about, among other things, how to protect plants from cold weather based on the first freeze date and the last freeze date of each year. For example, some plants need to be protected from cold weather in the winter or brought indoors. Other plants benefit from a "heeling-in" process prior to winter. Because of this the winterize schedule may differ between plants of different species and between plants of the same species located in different climatic regions. The text field is correlated to an action schedule used to calculate an action date when the text will be sent to a user. Table 3 below shows a preferred embodiment of a winterize schedule, instructions table.

TABLE 3

| Action Text | Action Schedule |
|---|---|
| Place plant outside | Last freeze date + 1 week |
| Place plant inside | First freeze date − 1 week |

Fertilizer schedule instructions table 341 includes a table having a text field in which is stored instructions about specific fertilizer action to be taken depending on the average first freeze date and last freeze date every year. In one embodiment, fertilizing begins just after the last freeze date in spring and then continues at regular intervals during the growing season, and ceases four weeks prior to the first freeze date in the fall. Table 4 below includes a preferred embodiment of a fertilizer schedule instructions table.

TABLE 4

| Action Text | Action Schedule |
|---|---|
| 1st Fertilize Action | Last freeze date + 7 days |
| 2nd Fertilize Action | Last freeze date + 4 weeks |
| 3rd Fertilize Action | Last freeze date + 8 weeks |
| 4th Fertilize Action | Last freeze date + 12 weeks |
| Last Fertilize Action | First freeze date − 1 month |

Pruning schedule instructions table 342 dictates when pruning should be done to the plant. In one embodiment, pruning can begin, depending on the plant, just before the last freeze date in the spring but must cease a certain number of weeks prior to the first freeze date in the fall. Pruning schedule instructions table 342 includes a text field correlated to an equation for calculating the corresponding action date based on the last freeze date and the first freeze date every year based on GPS location. Table 5 below shows a preferred embodiment of a pruning schedule instructions table.

TABLE 5

| Action Text | Action Schedule |
|---|---|
| 1st Pruning Action | Last freeze date − 7 days |
| 2nd Pruning Action | Last freeze date + 6 weeks |
| 3rd Pruning Action | First freeze date − 4 weeks |

Figure 5:
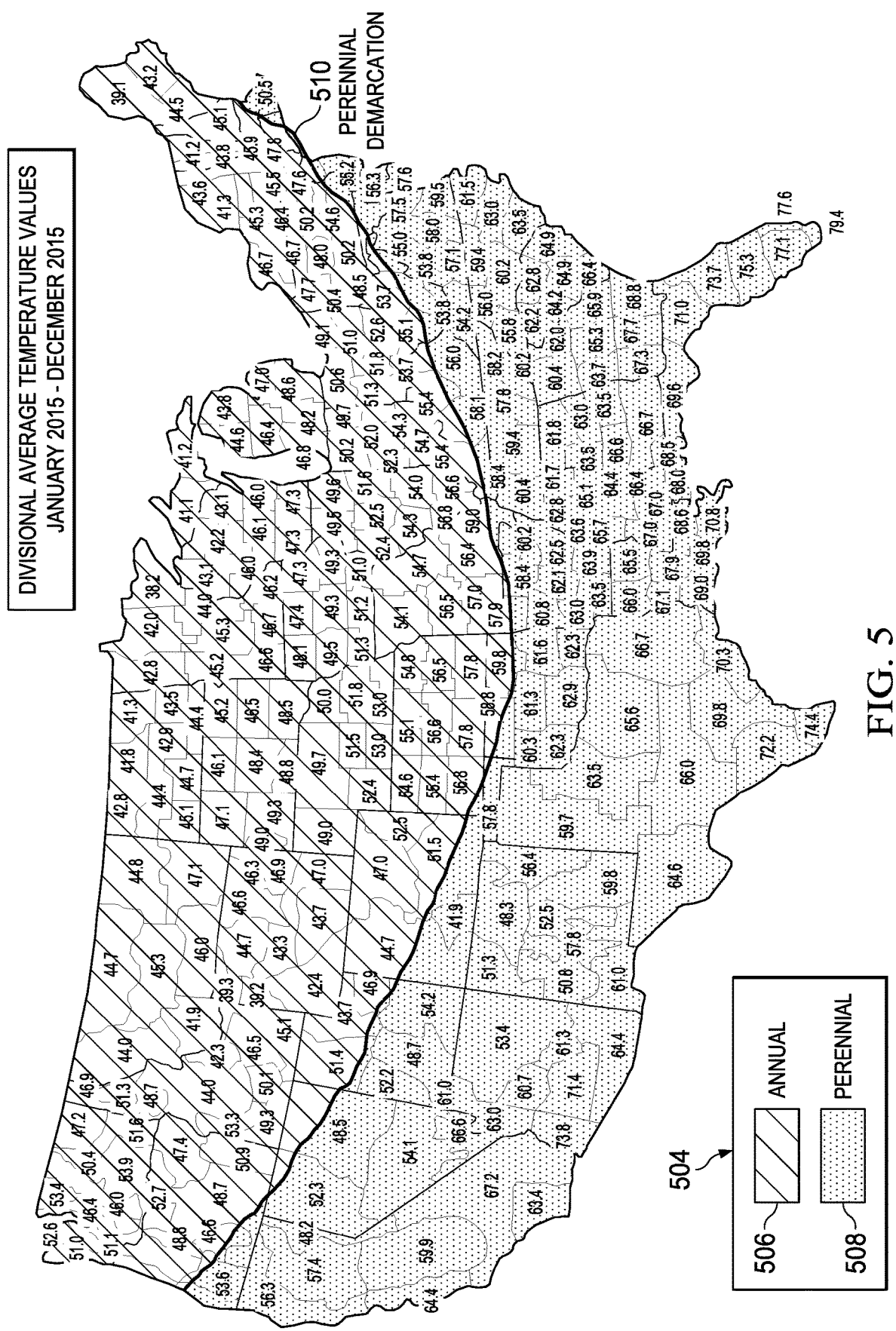
FIG. 5 shows a geographic map of the United States, including a perennial demarcation line, of a preferred embodiment of the disclosure.

Plant database 330 also includes perennial table 334. The perennial table uses GPS data to drive specific replanting instructions for each type of plant. In warmer regions, the plant may be perennial and hence not need to be replanted each year. In colder regions the plant may be annual and hence need to be replanted each year. For example, FIG. 5 is a map of average temperature values of the continental United States subdivided into divisions, with the temperature values coded by color to legend 504. Legend 504 lists the two divisions and designates them as 506, "annual" and 508 "perennial." The map shows a perennial demarcation line 510. The line shows, in general, the regions of the country where each plant is considered a "annual" and "perennial." The table is stored as a set of GPS coordinates associated with a "true" flag, indicating "perennial" at that GPS location or "false" flag indicating "annual" at that GPS location. In one embodiment, a table is stored in each plant record for each plant ID in the plant database. An example of the perennial table is shown in Table 6.

TABLE 6

| GPS Location | Perennial Type |
|---|---|
| 32.77°N, 96.79°W | True |
| ... | ... |
| 41.87°N, 87.62°W | False |

Plant data base 330 also includes fertilizer type table 333. The fertilizer type table uses GPS data to catalog specific fertilizing instructions for each type of plant. Different types of soils throughout the United States require different fertilizers in order to balance them for use with different types of plants. For example, soils in the Midwest have a high pH and therefore require higher phosphate and lower potash. Soils in the southern United States are lower pH and therefore require higher nitrogen, lower phosphate and higher potash. The table stored is a set of GPS coordinates associated with a fertilizer type including percentage nitrogen, percentage phosphate, percentage potash and a recommended vendor. In one embodiment, the table is stored in each plant record for each plant ID in a plant database. An example of the fertilizer type table 333 is shown in Table 7.

TABLE 7

| GPS Location | Fertilizer Type | Vendor |
|---|---|---|
| 32.77°N, 96.79°W | 26-0-10 | Scotts |
| ... | ... | ... |
| 41.87°N, 87.62°W | 5-2-0 | Micorganite |

Plant database 330 also includes NFC tag data 346. In a preferred embodiment, NFC tag data includes 4,096 bytes which is encoded with the plant ID or a unique number. The number is used to obtain further information about the plant, updated to reflect current climate conditions as will be further described. In another preferred embodiment, the NFC tag data is derived by a hash function using the plant ID number and the GPS coordinates of the location where the plant will be located when adult. The hash function may be a secure hash algorithm, such as SHA, SHA-1, SHA-2, SHA-3, and the like or a message digest algorithm, such as MD2, MD4, MD5, MD6, and the like.

Figure 3C:
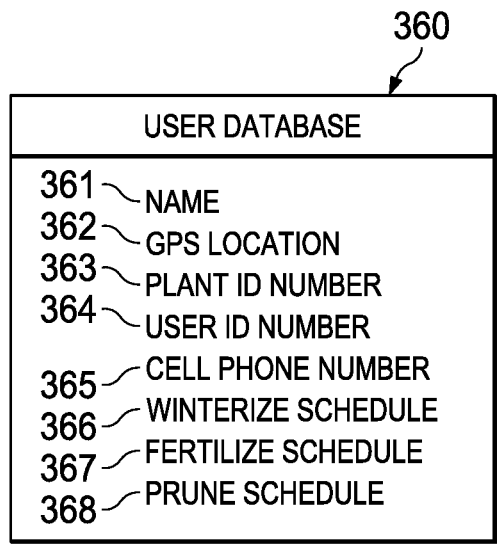
FIG. 3c shows a user database diagram in accordance with an embodiment of the disclosure.

Referring then to FIG. 3c, the user database 360 is described. User database 360 includes a record for each user. Each record includes a user name 361, a default user GPS location 362, one or more plant ID numbers 363, a user ID number 364, a user specific cell phone number 365, a user specific winterize schedule 366, a user specific fertilizer schedule 367 and a prune schedule 368.

Figure 3D:
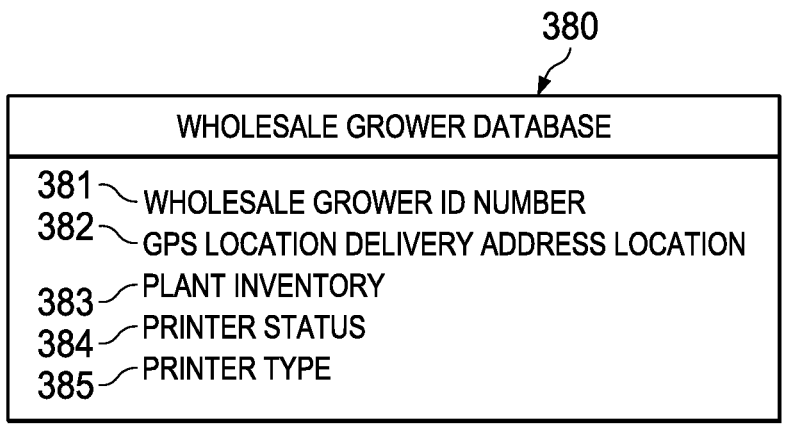
FIG. 3d shows a wholesale grower database diagram in accordance with an embodiment of the disclosure.

Referring then to FIG. 3d, a wholesale grower database 380 is described. Wholesale grower database 380 includes a record for each wholesale grower participating in the system. Each record includes a wholesale grower ID number 381, a set of GPS coordinates corresponding to the GPS location delivery address location 382, a plant inventory 383 including plant ID numbers, a printer status 384 and printer type 385.

Figure 3E:
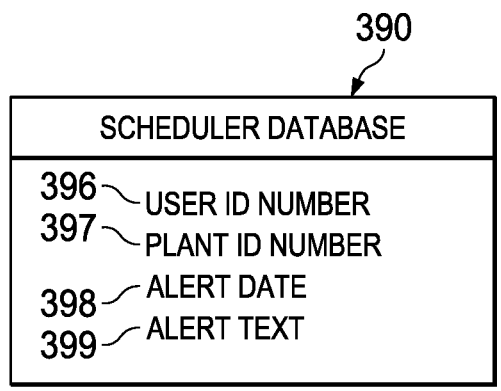
FIG. 3e shows a scheduler database diagram in accordance with an embodiment of the disclosure.

Referring to FIG. 3e, a scheduler database 390 is described. Scheduler database 390 includes a record for each user of the system that has an alert date scheduled. Each record present has a plant ID number 397. Scheduler database 390 has at least one alert date 398 and alert text 399. Each record corresponding to a user ID number 396 can have more than one plant ID. Similarly, each plant ID can have more than one alert date and alert text.

Figure 4A:
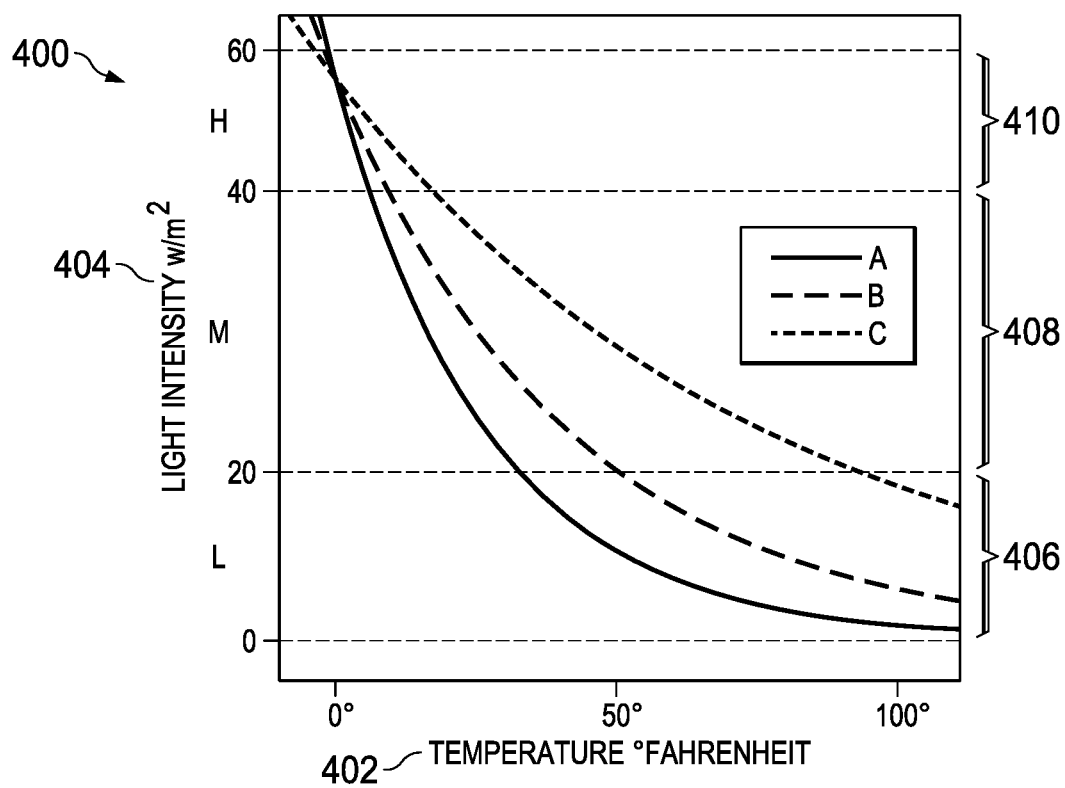
FIG. 4a shows a temperature versus light curve for a preferred embodiment of the disclosure.

Referring to FIG. 4a, a set of temperature versus light curves graph 400 is shown. Graph 400 shows three curves, "A", "B", and "C". Each curve represents an example of a normalized plot for an example light equation 331 for a specific plant having a record in the plant database 330. Along the x-axis is Temperature 402 in degrees Fahrenheit. Along the y-axis is relative light intensity 404, measured in w/m$^2$. The curves are modeled after exponential decay expressed as the following differential equation, where L is light intensity for each GPS location, T is the average maximum July temperature and λ is the exponential decay constant.

$$\frac{dL}{dT} = -\lambda L \qquad \text{Eq. 1}$$

The solution to this equation is:

$$L(T) = L_0 e^{-\lambda T} \qquad \text{Eq. 2}$$

In other embodiments, T can be the mean monthly temperature, the annual mean temperature, the mean extreme monthly temperature or the mean annual maximum temperature.

It has been determined that a decreasing exponential models the light requirements reasonably well for many plant species. For example, plot A shows a decay of $\lambda=3.7$ and serves as a good model for pteridophyte plants such as ferns. Plot B indicates a $\lambda=2.4$ and serves as a good model for magnoliophyta plants such as flowering plants. Plot C indicates a $\lambda=1.3$ and serves as a good model for caryophyllales plants such as cactus.

The light intensity axis is divided into three ranges. The low range 406 is between about 0-20 w/m$^2$, which correlates generally to 0 to 3 hours of light per day, the middle range 408 between about 20-40 w/m$^2$, which correlates generally to 3 to 6 hours of light per day, and the high range 410 between about 40-60 w/m$^2$ which correlates generally to 6 or more hours of light per day. The ranges are used as a means to summarize light requirements and are used in calculation of the plant guide number as will be further described.

Figure 4B:
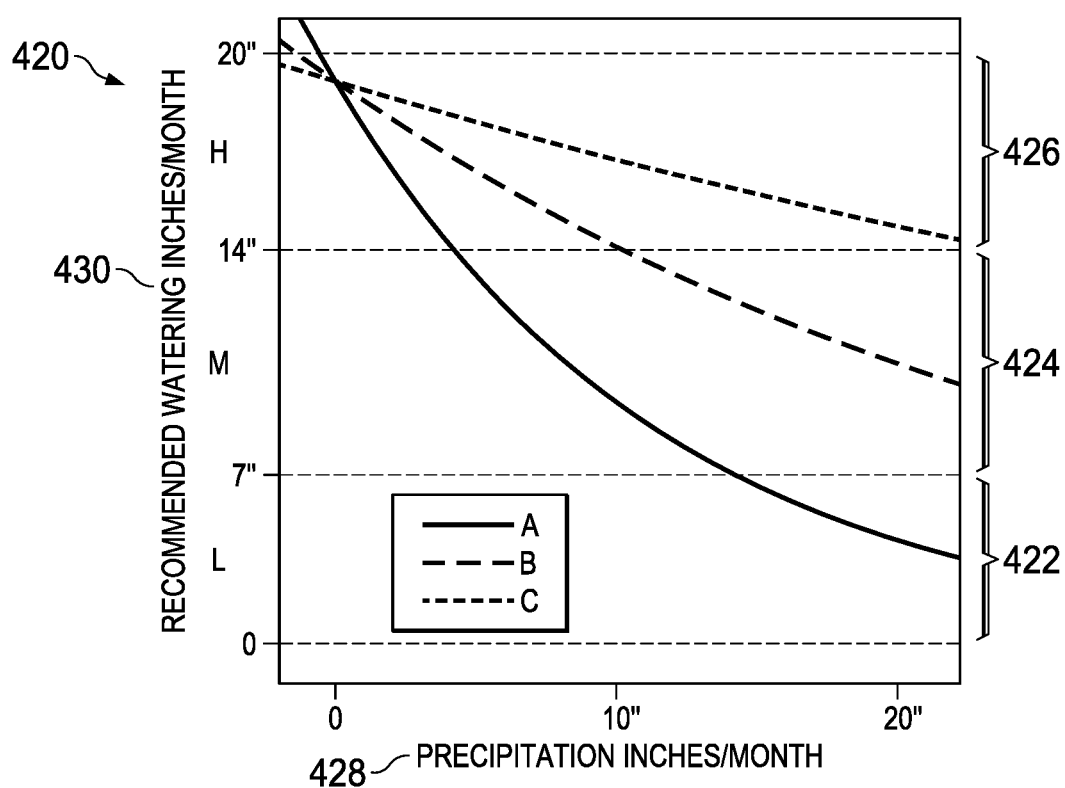
FIG. 4b shows a precipitation versus recommended watering curve for a preferred embodiment of the disclosure.

Referring then FIG. 4b, a set of precipitation versus recommended watering curves graph 420 are shown. Graph 420 shows three normalized curves, "A", "B", and "C". Each curve represents an example of a plot for an example of a water equation 332 for a specific plant having a record in the plant database 330. Along the x-axis is average monthly precipitation 428. Along the y-axis is the recommended water required 430, in inches per month. The curves are modeled on exponential decay.

The equation is:

$$W(R) = W_0 e^{-\lambda R} \qquad \text{Eq. 3}$$

Where W recommended watering in inches per month, R is average monthly precipitation and $\lambda$ is the exponential decay constant.

It has determined that a decreasing exponential models the watering requirements reasonably well for many plant species. For example, Plot A indicates a $\lambda=0.3$ and serves as a good model for plants which require very little water such as cactus. Plot B indicates a $\lambda=0.7$ and serves as a good model for plants which require moderate water such as maize or corn. Plot C shows a decay of $\lambda=1.7$ and serves as a good model for plants which require a large amount of water such as a canna or canna lily.

The y axis is divided into three ranges. The low range 422 is between about 0-7 in/mo, the middle range 424 is between about 7 and 14 in/mo and the high range 426 is between 14 and 20 in/mo.

Figure 6A:
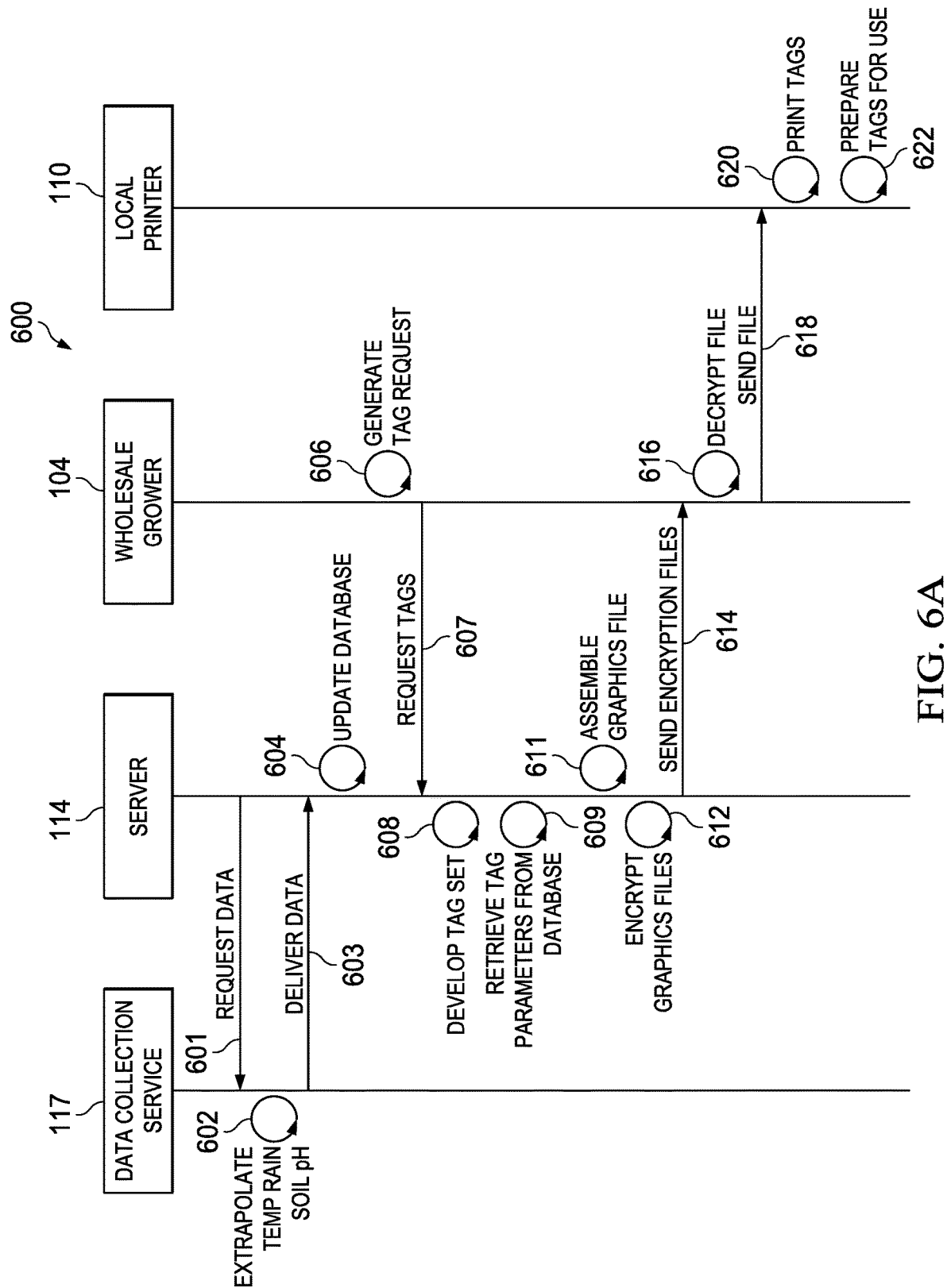
FIG. 6a is a data flow diagram of the print tags function in an embodiment in accordance with the disclosure.

Turning then to FIG. 6a, a data flow diagram of the system level functions for the print tags function of the system in a preferred embodiment is described. In this embodiment, the wholesale grower requests a certain number and type of durable plant tags from the server, which supplies them after updating the information required.

At step 601, server 114 requests updated data from data collection service 117. At step 602, data collection service extrapolates temperature data, precipitation data and soil alkalinity for each set of GPS coordinates in the United States from known empirical measurements. At step 603, data collection service 117 delivers the data to server 114. At step 604, server 114 updates all records in climate database 300, and the perennial table in plant database 330, as will be further described.

At step 606, wholesale grower 104 generates an inventory listing of plants for which tags are required. The inventory listing includes a plant ID number and number of plants in inventory for each plant ID number. At step 607, wholesale grower 104 transmits the inventory listing along with a request for tags to server 114.

At step 608, server 114 locates the appropriate graphics design files for each plant ID contained in the request. At step 609, one or more tag parameters are retrieved from memory. In one embodiment, the graphics files and tag parameters are retrieved from database 124. At step 611, a tag graphic file is assembled. In one embodiment, the tag graphic file includes an icon with the plant guide number and icon color, a picture of the plant, and additional data and horticultural information about the plant, as shown by way of example, in durable plant tags 226 and 236 of FIG. 2a. To derive the plant guide number, the server first queries the plant database to determine if a plant guide number is located in the record that corresponds to the plant ID. If so, that is the plant guide number reported. If not, the plant guide number is derived as set out in relation to FIG. 6b. In one embodiment, the front side of the durable plant tag and the back side of the durable plant tag are both incorporated into a single file. Suitable file formats include Portable Document Format (PDF), Encapsulated PostScript (EPS), Joint Photographic Experts Group (JPG), Tagged Image File Format (TIFF), Graphics Interchange Format (GIF), Portable Network Graphics (PNG), and so on.

At step 612, server 114 encrypts the graphic files. In one preferred embodiment, DES encryption is employed. At step 614, server 114 sends the encrypted graphic files to wholesale grower 104. At step 616, wholesale grower 104 decrypts the files. In a preferred embodiment, in order to decrypt the files, wholesale grower 104 must supply a password and a cypher key which can be set to expire after a certain number of print cycles. At step 618, wholesale grower 104 sends the decrypted files to second printer 110. At step 620, the local printer prints the tags. At step 622, the tags are separated and prepared for use. In a preferred embodiment the encryption and decryption of the graphic files is accomplished by "Photo Tag Express" brand software available from Brothersoft.

After the durable plant tags are printed, they are installed by the wholesale grower. The durable plant tags are installed or packaged with the plants that are to be displayed at retailer 106. In one embodiment, since the durable plant tags are location specific, they are installed on plants that match the final destination of the plant.

Figures 1, 6B:
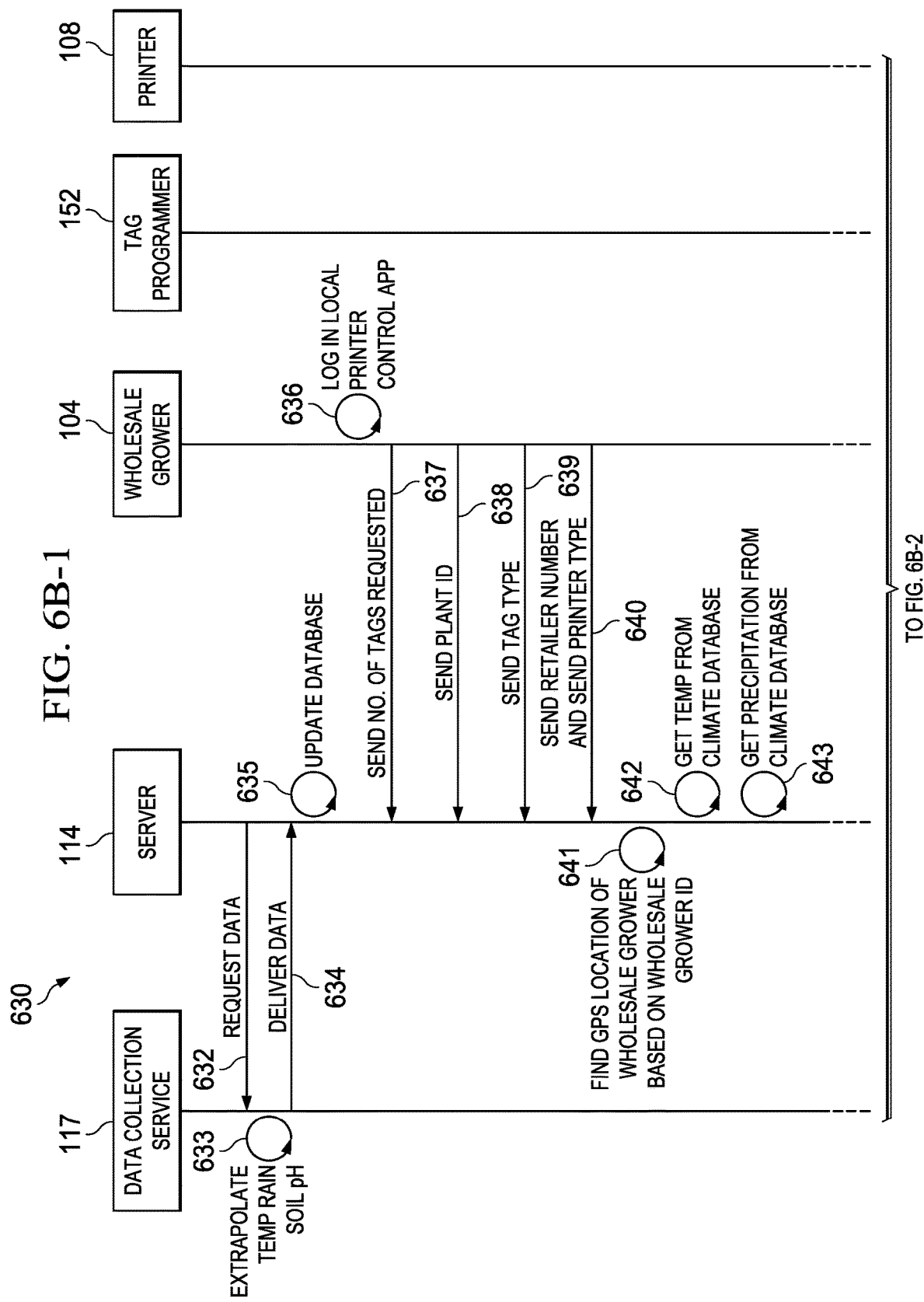
Figures 2, 6B:
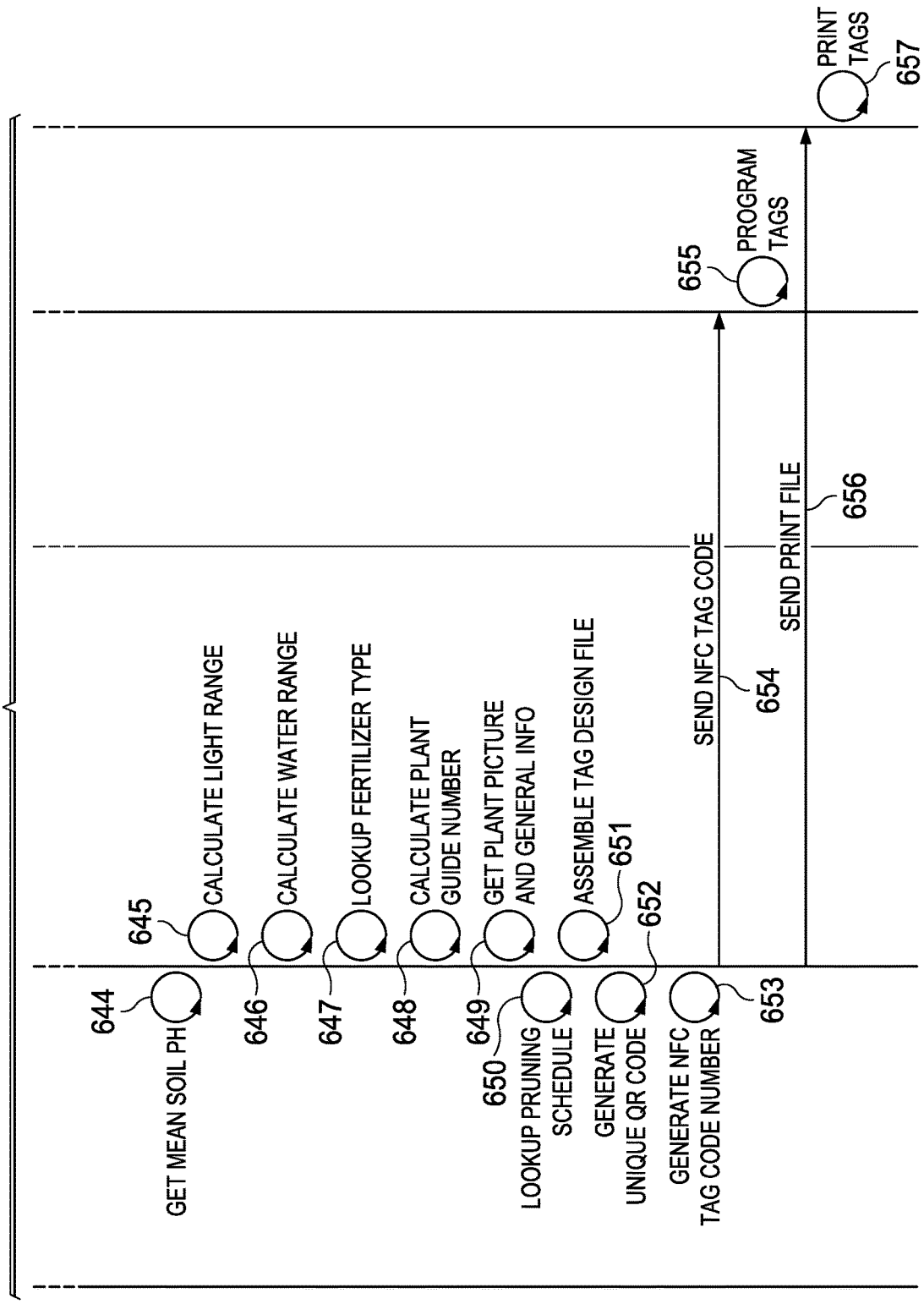

Turning then to FIG. 6b a data flow diagram of the print GPS specific tags function of the system of a preferred embodiment is shown. In this embodiment, the information on the durable plant tag, including the icon and plant guide number, is generated for a specific type of plant and for a specific geographic region.

As step 632, server 114 requests updated data from data collection service 117. At step 633, data collection service 117 extrapolates temperature, precipitation and soil pH for each set of GPS coordinates in the United States from known empirical data. At step 634, data collection service 117 delivers the information to server 114. At step 635, server 114 updates the climate database 300 and the perennial table of plant database 330.

At step 636, wholesale grower 104 logs into local printer control application, as will be further described. At step 637, wholesale grower 104 sends a number of tags requested to server 114. At step 638, wholesale grower 104 sends a set of plant ID's to server 114. At step 639, wholesale grower 104 sends a tag type requested to server 114. At step 640, wholesale grower 104 sends the wholesale grower ID number and the printer type and status to server 114.

At step 641, server 114 queries wholesale grower database 380 to identify the record that corresponds to the wholesale grower ID number. Server 114 then queries the database to determine the GPS coordinates associated with the wholesale grower ID number in the record. This GPS location is assumed to be the geographic location where the plant will be located when mature. In another embodiment, the GPS coordinates are supplied by the wholesale grower for the location where the plant will be located when mature. This is important in cases where plants, such as roses, are grown in one location and shipped to distant locations where they will be planted. In this case, the durable plant tag must match the final location of the plant, not the location of the wholesale grower.

At step 642, server 114 queries climate database 300 to identify the mean high July temperature, or target temperature, associated with the GPS location. In a similar way, at step 643, server 114 uses the GPS coordinates supplied to retrieve the associated mean precipitation value, or target precipitation, from climate database 300. At step 644, server 114 uses the GPS coordinates to retrieve the mean soil pH associated with the GPS coordinates from climate database 300.

At step 645, server 114 accesses the light equation in plant database 330 for the specific plant ID. The mean July average maximum temperature for the GPS location is substituted into the equation to arrive at a corresponding light intensity. The light intensity is then ranked, low, medium or high according to the corresponding ranges provided by the equation as previously described.

At step 646, server 114 accesses the water equation for the specific plant ID in plant database 330. The average precipitation value for the GPS location is substituted into the water equation to derive the corresponding monthly watering value. The required watering value is then ranked low, medium or high according to the ranges, as previously described.

At step 647, server 114 accesses the fertilizer type table in the plant database for the record corresponding to the plant ID. The fertilizer type is calculated by inserting the GPS location in the table and locating the corresponding fertilizer type and vendor. The fertilizer type and vendor are returned.

At step 648, server 114 calls a function to calculate a plant guide number based on the results of steps 645, 646 and 647. That function is described more completely with reference to FIG. 6c.

At step 649, the server queries plant database 330 to retrieve the picture of the plant and other general information. In a preferred case, the general information is obtained by sending a query to the plant database to retrieve the text of the general information, or target information, that corresponds to the GPS coordinates provided. In this way, each durable plant tag will be customized with information that is relevant both for the type of plant and the location where it will be grown when mature. At step 650, the server looks up the pruning schedule as will be further described. At step 651, the plant guide number, icon, picture, general information, fertilizer information, QR code, and pruning schedule are assembled into a tag design file. In an alternate embodiment, the information includes a tag template. The tag template is a file that defines how the information is to be arranged on each specific tag type.

At step 652, server 114 generates a unique QR code. In a preferred embodiment, server 114 encodes the plant ID into the QR code. The QR code is unique for each type of plant and can include a GPS component.

At step 653, server 114 encodes NFC tag with the same unique number. At step 654, server 114 sends the NFC tag code to tag programmer 152. At step 655 tag programmer 152 generates a radio frequency signal which is accepted by NFC tag 127 and used to encode the tag with the unique number. In a preferred embodiment, each NFC tag is then locked or "burned" to prevent reprogramming. At step 656, server 114 sends the tag design file to first printer 108. At step 657, printer 108 prints the durable plant tag. In an alternate embodiment, the order of steps 655 and 657 may be reversed.

Figure 6C:
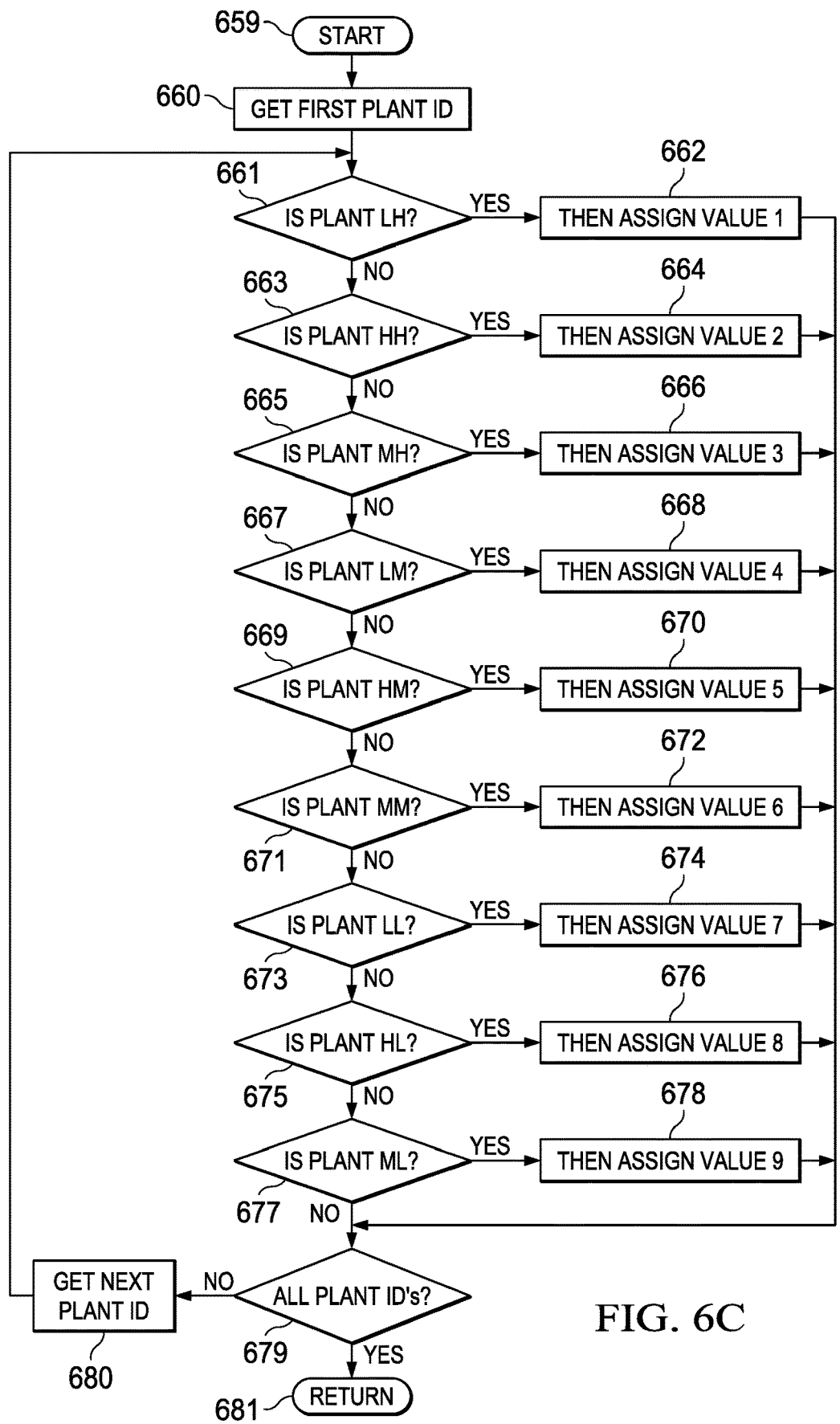
FIG. 6c is a flowchart of a process for deriving a plant guide number in one embodiment in accordance with the disclosure.

FIG. 6c is a flow chart of the process for deriving a plant guide number for a durable plant tag as required by step 648.

At step 659, the process starts.

At step 660, a plant ID is selected from a list of one or more plant ID's.

At step 661, it is determined if the currently selected plant requires a low level of moisture and a high level of light (LH). If the currently selected plant requires a low level of moisture and a high level of light (LH), then the process proceeds to step 662. If the currently selected plant does not require a low level of moisture and a high level of light (LH), then the process proceeds to step 663.

At step 662, the process assigns a value of 1 for the plant guide number and a color of dark blue for the icon for the currently selected plant and the process proceeds to step 679.

At step 663, it is determined if the currently selected plant requires a high level of moisture and a high level of light (HH). If the currently selected plant requires a high level of moisture and a high level of light (HH), then the process proceeds to step 664. If the currently selected plant does not require a high level of moisture and a high level of light (HH), then the process proceeds to step 665.

At step 664, the process assigns a value of 2 for the plant guide number a color of light brown for the icon and the process proceeds to step 679.

At step 665, it is determined if the currently selected plant requires a medium level of moisture and a high level of light (MH). If the currently selected plant requires a medium level of moisture and a high level of light (MH), then the process proceeds to step 666. If the currently selected plant does not require a medium level of moisture and a high level of light (MH), then the process proceeds to step 667.

At step 666, the process assigns a value of 3 for the plant guide number and a color of dark green for the icon and the process proceeds to step 679.

At step 667, it is determined if the currently selected plant requires a low level of moisture and a medium level of light (LM). If the currently selected plant requires a low level of moisture and a medium level of light (LM), then the process proceeds to step 668. If the currently selected plant does not require a low level of moisture and a medium level of light (LM), then the process proceeds to step 669.

At step 668, the process assigns a value of 4 for the plant guide number and a color of light green to the icon and the process proceeds to step 679.

At step 669, it is determined if the currently selected plant requires a high level of moisture and a medium level of light (HM). If the currently selected plant requires a high level of moisture and a medium level of light (HM), then the process proceeds to step 670. If the currently selected plant does not require a high level of moisture and a medium level of light (HM), then the process proceeds to step 671.

At step 670, the process assigns a value of 5 for the plant guide number and a color of red to the icon and the process proceeds to step 679.

At step 671, it is determined if the currently selected plant requires a medium level of moisture and a medium level of light (MM). If the currently selected plant requires a medium level of moisture and a medium level of light (MM), then the process proceeds to step 672. If the currently selected plant does not require a medium level of moisture and a medium level of light (MM), then the process proceeds to step 673.

At step 672, the process assigns a value of 6 for the plant guide number and a color of light blue to the icon and the process proceeds to step 679.

At step 673, it is determined if the currently selected plant requires a low level of moisture and a low level of light (LL). If the currently selected plant requires a low level of moisture and a low level of light (LL), then the process proceeds to step 674. If the currently selected plant does not require a low level of moisture and a low level of light (LL), then the process proceeds to step 675.

At step 674, the process assigns a value of 7 for the plant guide number and a color of magenta to the icon and the process proceeds to step 679.

At step 675, it is determined if the currently selected plant requires a high level of moisture and a low level of light (HL). If the currently selected plant requires a high level of moisture and a low level of light (HL), then the process proceeds to step 676. If the currently selected plant does not require a high level of moisture and a low level of light (HL), then the process proceeds to step 677.

At step 676, the process assigns a value of 8 for the plant guide number and a color of blue green to the icon and the process proceeds to step 679.

At step 677, it is determined if the currently selected plant requires a medium level of moisture and a low level of light (ML). If the currently selected plant requires a medium level of moisture and a low level of light (ML), then the process proceeds to step 678. If the currently selected plant does not require a medium level of moisture and a low level of light (ML), then the process proceeds to step 679.

At step 678, the process assigns a value of 9 for the plant guide number and a color of pink to the icon and the process proceeds to step 679.

At step 679, it is determined if all of the plants of the list of identified plants have been processed. If all of the plants have been processed, then the process proceeds to step 681 and ends. If more plants still need to be processed, then the process proceeds to step 680.

At step 680, the next plant ID from the list of plant IDs is selected to be processed and the process returns to step 661.

Figure 7:
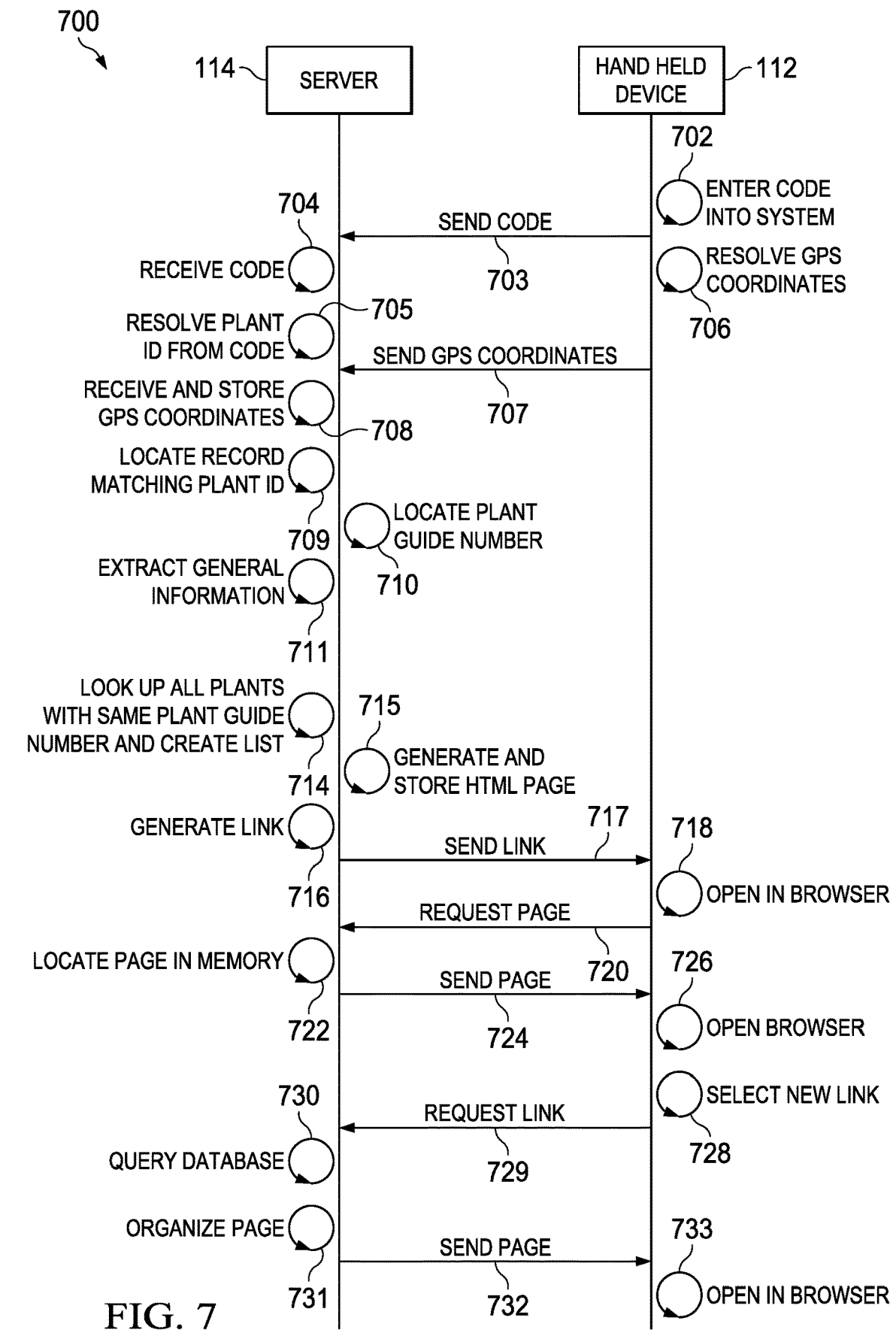
FIG. 7 is a data flow diagram of the get all similar plants and care instructions functions in an embodiment in accordance with the disclosure.

Referring then to FIG. 7 a data flow diagram showing a preferred embodiment of the get all similar plants and care instructions function of the system in a preferred embodiment will be described. In this embodiment, the system locates all similar plants in the plant database that share the same plant guide number to assist in choosing plants that will grow well together in a particular geographic location.

At step 702, hand held device 112 creates an SMS text message including a unique number from which the plant ID may be derived. In one embodiment, the number is a simple 6 digit integer. In another embodiment, the unique number can be the plant ID. In another embodiment, the unique number includes a hash of the GPS coordinates of the plant location and the plant ID. In an alternate embodiment, the hand held device scans the printed QR or bar code and then resolves it into a URL containing the plant ID or unique number. In an alternate embodiment, hand held device 112 deploys a near field communication signal in the vicinity of a plant tag which includes an NFC tag embedded in it. The NFC tag embedded in the plant tag returns data when scanned. The data is resolved into a URL containing the plant ID or other unique number. In another embodiment, the data is resolved by the hand held device into both the plant ID number and the GPS location of the plant. This GPS location is then assumed to be the location of the plant when mature. This embodiment is useful when the hand held device is not capable or willing to provide its GPS location or when a GPS signal is not available.

At step 703, hand held device 112 sends an SMS message including a unique number to server 114. In an alternate embodiment of step 703, hand held device 112 requests an HTML webpage by opening a URL derived from the printed code.

At step 704, server 114 receives the unique number. In an alternate embodiment of step 704, server 114 receives the request for an HTML page and decodes it to derive the plant ID.

At step 705, the server receives the unique number and compares it to a lookup table to derive a corresponding plant ID number.

At step 706, hand held device 112 resolves its GPS coordinates, if possible. If not, the location is resolved from the QR code or NFC location data. At step 707, hand held device 112 sends its GPS coordinates to server 114. At step 708, server 114 receives and stores the GPS coordinates. In another preferred embodiment, hand held device 112 may provide a zip code as an alternative for the GPS coordinates. The zip code can be resolved into a range of GPS coordinates from which GPS coordinates central to the zip code area are chosen by server 114 as the GPS coordinates. In an alternate embodiment of step 708, server 114 uses the GPS supplied by the wholesale plant manufacturer.

At step 709, server 114 access the plant database and locates the record which matches the plant ID. At step 710, server 114 then locates the plant guide number in the data record.

At step 711, server 114 extracts the general information from the plant database for the plant record associated with the plant ID. In one preferred embodiment, the GPS coordinates are used to access the general information table and retrieve the general information that is specific for the GPS coordinates supplied.

At step 714, server 114 queries the plant database for all records which include the same plant guide number and creates a list of pointers to the associated records. At step 715, server 114 generates an HTML page including the general information and the list of the plant records in the plant database which have the same plant guide number and stores it in a memory location.

At step 716, server 114 generates a URL in the form of a link which includes the pointers to the memory locations. At step 717, the link is sent to hand held device 112 in the form of an SMS message.

At step 718, user device 112 opens the SMS message and clicks on the link. The link is displayed in an application running on hand held device 112 after receiving the text message from server 114. In one embodiment, the application is a browser opened on hand held device 112 which generates an HTTP GET request using the link received in the text message. At step 720, the hand held device requests the page from the server that includes the list of plant guide numbers and the general care information for each plant on the list. At step 722, the server locates the requested page in memory. At step 724, the page is returned to hand held device 112.

At step 726, the page is displayed by the hand held device 112. At step 728, the hand held device 112 and may click on any one plant record included in the list in order to request information about any of the plants on the list. The plant records are represented by additional links to alternate web pages. At step 729, the page for the additional plant is requested by the hand held device 112. At step 730, the server 114 receives the request and queries the database using the plant ID of the plant record requested. At step 731, the server 114 organizes the new HTML page. At step 732, the server 114 sends the page to the hand held device 112. At step 733, the hand held device 112 renders the page and displays information about the requested plant or plants.

Figure 8:
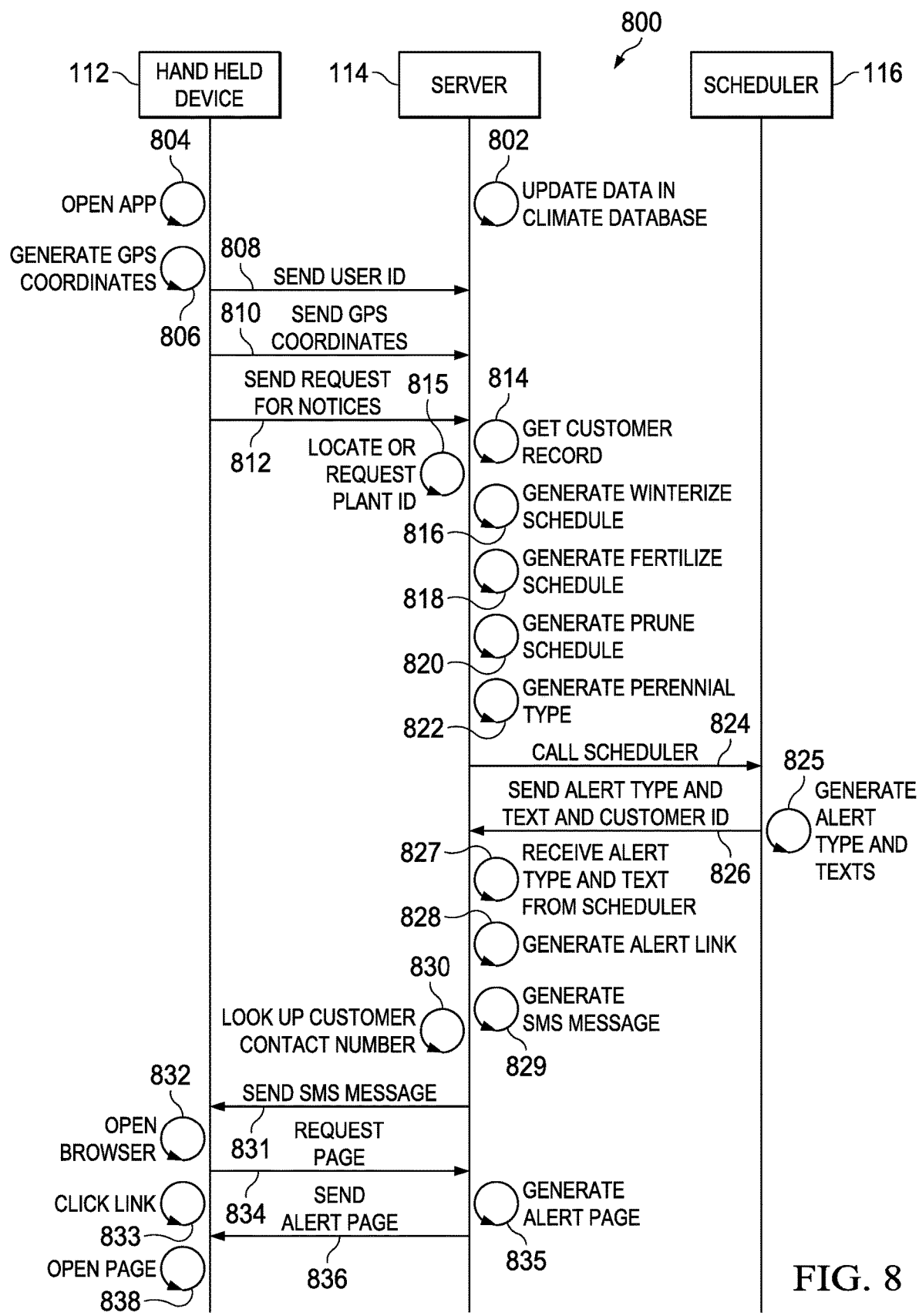
FIG. 8 is a data flow diagram of the push notice and instructions function in an embodiment in accordance with the disclosure.

Referring then to FIG. 8 a data flow diagram for the push notice and instructions function of a preferred embodiment will be described. In this embodiment, electronic notices are sent to the hand held device on certain dates that include geographically specific plant care instructions.

At step 802, server 114 updates the climate database by regenerating temperature, precipitation and soil pH data as described in relation to FIG. 6a. At step 804, hand held device 112 opens an application as will be further described. At step 806, hand held device 112 generates a set of GPS coordinates representing its location. At step 808, hand held device 112 sends its user identification number to server 114. At step 810, hand held device 112 sends its GPS coordinates to server 114. At step 812, hand held device 112 sends a request for push notices and instructions.

At step 814, server 114 accesses user database 360 to locate the record corresponding to the user ID number. At step 815, the server locates a plant ID owned by the user in the record. In an alternate embodiment, if there is no plant ID in the record, the server sends a request to the user to scan the durable plant tag or to otherwise identify the plant ID. At step 816, server 114 generates a winterize schedule as will be further described. At step 818, server 114 generates a fertilize schedule as will be further described. At step 820, server 114 generates a prune schedule as will be further described. At step 822, server 114 generates a perennial type as will be further described. At step 824, server 114 calls the scheduler. At step 825, scheduler 116 implements the winterize schedule, fertilize schedule and prune schedule. At step 825, the scheduler 116 generates an alert type and an alert text. In a preferred embodiment, the alert type can be one or more of a winterize alert, a fertilize alert and a prune alert. The alert body includes instructions as to an action to be taken and a date for the action to be completed. At step 826, the scheduler 116 sends the alert type and text to the server 114 along with the customer ID of the customer with which the alert is associated.

At step 827, server 114 receives an alert type and text from the scheduler along with the associated user ID. At step 828, server 114 generates an alert link based on the alert type and text data received. At step 829, server 114 generates an SMS message including the alert link. At step 830, the server 114 queries the user database to locate the record that corresponds to the user ID number. Once returned, the server retrieves the user phone number from the record. At step 831, server 114 sends an SMS including the alert link to hand held device 112 using the phone number.

At step 832, hand held device 112 opens a browser. At step 833 the hand held device clicks on the alert link in the SMS message. At step 834, hand held device 112 requests an HTML page from server 114 according to the link. At step 835, server 114 generates an HTML page including the alert type and text received from the scheduler. At step 836, server 114 sends the HTML alert page to hand held device 112. At step 838, hand held device 112 opens the alert page in a web browser.

Figure 9:
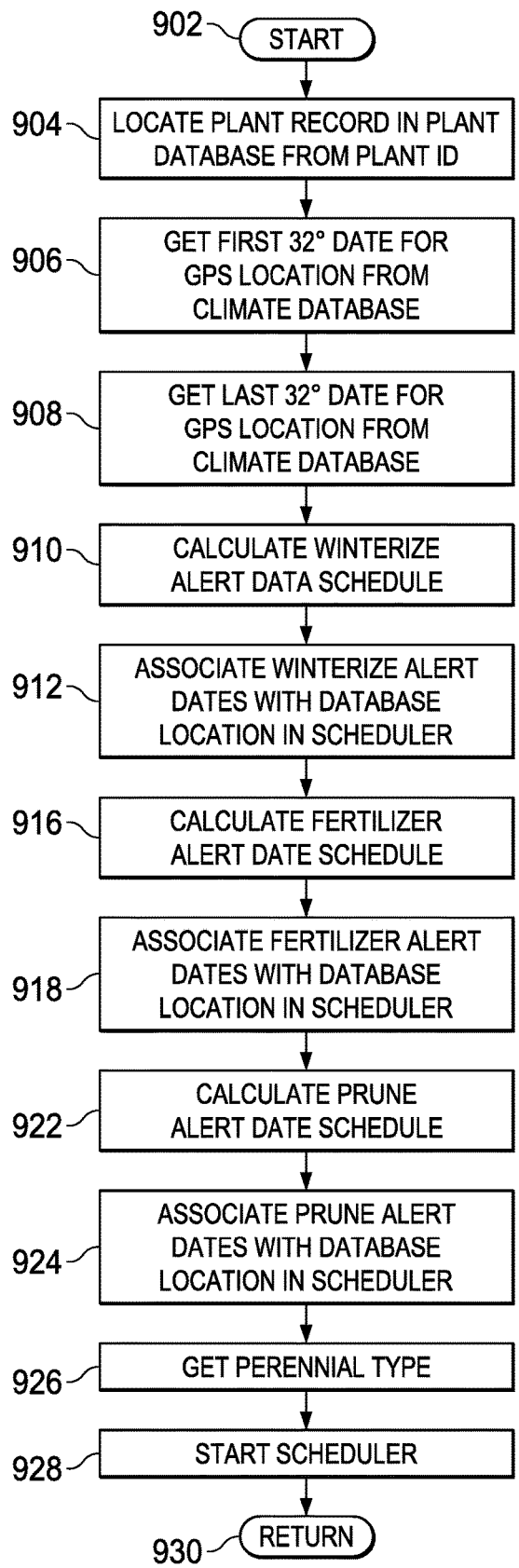
FIG. 9 is a flow chart of the generate schedules and perennial type functions in an embodiment in accordance with the disclosure.

Referring then to FIG. 9, a function of a preferred embodiment that implements steps 816, 818, 820, and 822 to generate the winterize schedule, the fertilize schedule, the prune schedule, and perennial type respectively, for each user will be further described.

At step 902, the function begins. At step 904, the function locates a plant record in the plant database according to the plant ID number.

At step 906, the function accesses climate database 300 and retrieves the first 32 degree Fahrenheit date for the record corresponding to the GPS location received. This date corresponds generally to the first freeze in the fall for each specific GPS location.

At step 908, the function accesses climate database 300 and retrieves the last 32 degree Fahrenheit date for the record corresponding to the GPS location received. The date corresponds generally to the last freeze in the spring for each specific GPS location.

In step 910, the function calculates the winter care alert date schedule. In a preferred embodiment, this step is accomplished by accessing the winter care schedule/instructions table in the record corresponding with the plant ID number in the plant database. The table, such as shown in Table 3, includes a column with text instructions corresponding to a schedule calculation equation. The first 32 degree Fahrenheit date and the last 32 degree Fahrenheit date for the GPS coordinates of the user are substituted into the corresponding winter care schedule equations. The equations add or subtract days as required to arrive at an action date. The action date and the text instructions are returned.

At step 912, the winterize alert schedule is stored in a database in the scheduler.

At step 916, the function calculates the fertilize alert date schedule. In a preferred embodiment, this step is accomplished by accessing the fertilizer schedule/instructions table in the record corresponding with the plant ID number in the plant database. The fertilize schedule, such as shown in Table 4, includes a column with text instructions corresponding to a schedule calculation equation. The first 32 degree Fahrenheit date and the last 32 degree Fahrenheit date for the GPS coordinates of the user are substituted into the corresponding fertilizer schedule equations. The equations add or subtract days as required to arrive at an action date. The action date and the text instructions are returned.

At step 918, the fertilize alert date schedule is stored in a database in the scheduler corresponding to the user ID number.

At step 922, the function calculates the prune alert date schedule. In a preferred embodiment this step is accomplished by accessing the prune schedule instructions table in the record corresponding with the plant ID number in the plant database. The pruning schedule, such as shown in Table 5, includes a column with text instructions corresponding to a schedule calculation equation. The first 32 degree Fahrenheit date and the last 32 degree Fahrenheit date are substituted into the corresponding pruning schedule equations. The equations add or subtract days as required to arrive at an action date. The action date and text instructions are returned.

At step 924, the prune alert date schedule is stored in a database in the scheduler corresponding to the user ID number.

At step 926, the function calculated the perennial type as follows. The function accesses the perennial table in the plant database for the record corresponding to the plant ID number. The function locates the GPS coordinates supplied by the hand held device in the perennial table for the specific plant ID and returns to corresponding state of "true" or "false." The perennial type, once determined, is stored in a database in the scheduler corresponding to the customer ID number.

At step 928, the scheduler is started. The scheduler loops, sending alerts and messages which correspond to alert dates for each customer ID and phone number until stopped. At step 930, the function returns.

Figure 10:
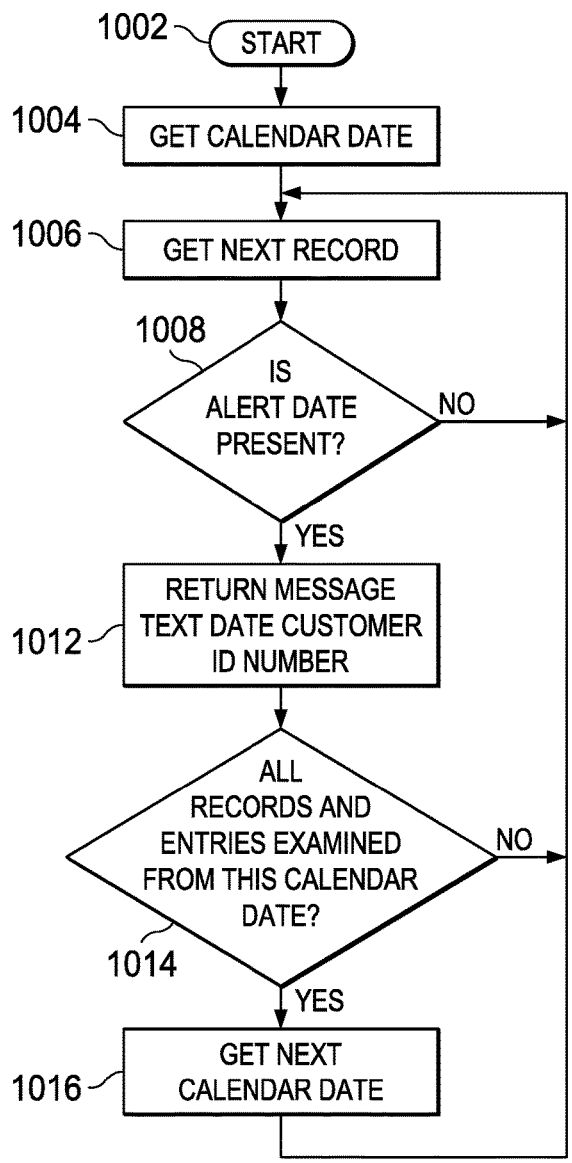
FIG. 10 is a flow chart of the scheduler functions in an embodiment in accordance with the disclosure.

Referring then to FIG. 10, the scheduler is described. At step 1002, the scheduler is started. At step 1004, the scheduler gets the current calendar date from server memory. At step 1006, the scheduler gets the next user record in the scheduler database. At step 1008, the scheduler compares the calendar date to the alert dates in the user record to determine if a match is present. If not, scheduler returns to step 1006. If so, the scheduler moves to step 1012.

At step 1012, the scheduler returns the message text associated with the alert date, the alert date and the customer ID associated with the alert date. At step 1014, the scheduler then checks to see if all records have been examined. If not, the scheduler returns to step 1006. If so, the scheduler moves to step 1016.

At step 1016, the scheduler gets the next calendar date and returns to step 1006. Unless interrupted, the scheduler runs continuously.

Figure 11A:
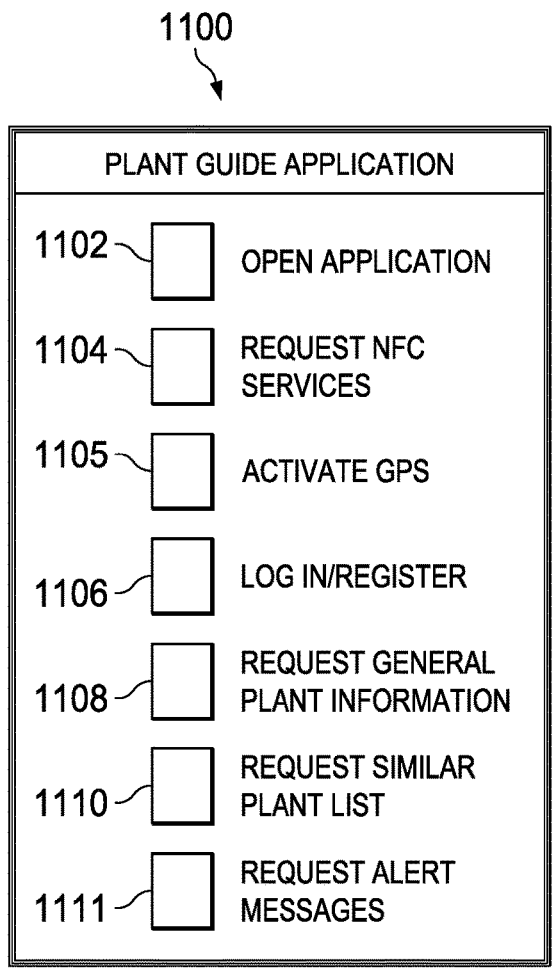
FIG. 11a shows an app screen of a preferred embodiment.

Referring then to FIG. 11a, operational screens of an app resident on hand held device 112, as used in relation to FIG. 7 will be described.

App screen 1100, provides the graphic user interface for the control functions of a user app resident on hand held device 112. Control 1102 provides a control to open the application and begin operation of its functions. Control 1104 allows the app to request activation of NFC services that are resident on the hand held device. Control 1105 allows the hand held device to activate its GPS receiver. Control 1106 allows the user to login and register with the system resident on server 114. In a preferred embodiment registration can include a password and a user ID for user identification. Control 1108 allows the hand held device to request general plant information from server 114 related to a plant ID. Control 1110 allows the hand held device to request plants with the same group number as that of the plant related the plant ID number. Control 1111 allows the hand held device to request an alert message.

Figure 11B:
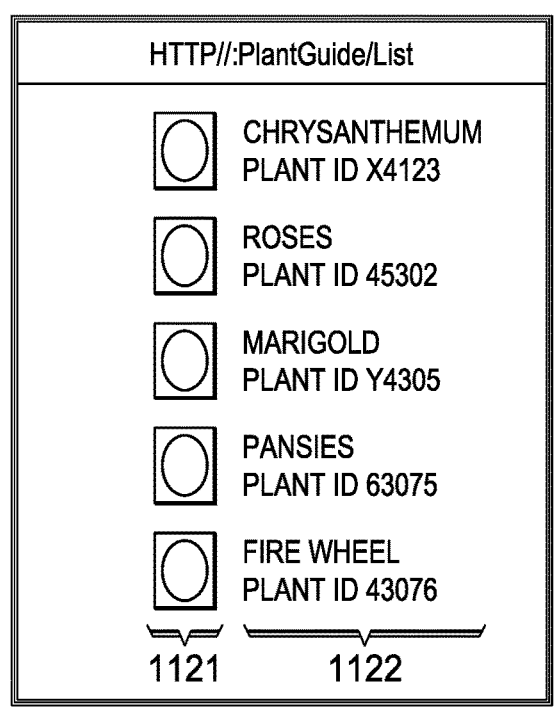
FIG. 11b shows an app screen of a preferred embodiment.

Referring then to FIG. 11b, the control screen for a preferred embodiment of an app resident on hand held device 112 is shown. In this case, the control screen is result of the page sent as step 764 from server 114 to hand held device 112 and rendered at step 765 of FIG. 7b.

Screen 1120 presents two columns of information, column 1121 includes a graphic for each plant from picture 338 in plant database 330. Column 1122 provides a corresponding plant name 336 and plant ID number 335 from plant record in the plant database.

It will be appreciated by those skilled in the art that the described embodiments disclose significantly more than an abstract idea including technical advancements in the field of data processing and a transformation of data which is directly related to real world objects and situations in that the disclosed embodiments enable a computer to operate more efficiently. For example, the disclosed embodiments transform positions, orientations, and movements of durable plant tags as well as transforming one or more servers and hand held devices from one state to another state.

It will be appreciated by those skilled in the art that modifications can be made to the embodiments disclosed and remain within the inventive concept. Therefore, this invention is not limited to the specific embodiments disclosed, but is intended to cover changes within the scope and spirit of the claims.

The invention claimed is:

1. A system for selecting different types of plants suitable for planting and growth in geographic-specific horticultural conditions, the system comprising:
   a durable plant tag associated with a first plant of a first plant type, the durable plant tag including horticultural data with at least one climate condition and with at least one soil condition suitable for planting and growth of the first plant, the durable plant tag comprising:
      at least one of an image, text, data, and horticultural information related to the first plant type, the image being of a plant of the first plant type in a mature stage of growth;
      a quick response (OR) code encoded with a unique identifying number, the identifying number being used to obtain additional information about the first plant type; and
      an icon including a symbol that summarizes selected horticultural characteristics of the first plant type, the icon including at least a plant guide number associated with information related to geographic-specific horticultural conditions based on geographic location data, the plant guide number including a light requirement component for the first plant type and a water requirement component for the first plant type, the icon being encoded with at least one of a light value, watering value and an icon color or icon shape associated with the plant guide number,
      wherein plant types with icons having the same icon color or icon shape and same plant guide number require similar light levels and watering levels and will grow successful in the same geographic locations;
   a hand held device, having a first processor and a first memory, the hand held device configured to read the OR code;
   a server having a second processor and a second memory, connected over a network to the hand held device;
   a first set of instructions stored in the first memory which when executed by the first processor cause the hand held device to:
      read the OR code from the durable plant tag;
      the durable plant tag co-located with the first plant, the first plant available for sale at a retailer facility;
      send the OR code read from the durable plant tag to the server;
      identify a set of geographic location data associated with the location of the hand held device;
      send the set of geographic location data to the server;
   a second set of instructions stored in the second memory, which when executed by the second processor cause the server to:
      receive the OR code read from the durable plant tag;
      derive a first plant ID uniquely identifying the first plant type for the first plant from the code;

receive the geographic location data associated with the location of the handheld device;

derive the plant guide number from the first plant ID and the geographic location data;

identify at least a second plant ID associated with the plant guide number, the second plant ID uniquely identifying a second plant type for a second plant from the code, where the first plant ID is different from the second plant ID and the first plant type is different from the second plant type;

the second plant available via a wholesale grower;

locate a set of plant information related to the second plant and also related to the plant guide number such that the second plant is compatible with the geographic location, the second plant having climate conditions and soil conditions compatible with the first plant suitable for planting and growing in the same climate and planting conditions as the first plant in the geographic-specific horticultural conditions including the same light requirement component for the first plant and the same water requirement component for the first plant; and send an identification of the second plant and at least one plant information for the second plant from the set of plant information to the hand held device.

2. The system of claim 1 wherein the durable plant tag further comprises an electronic tag and wherein the code further comprises a near field communications (NFC) signal communicated from the electronic tag to the hand held device.

3. The system of claim 2, wherein the near field communications (NFC) tag is uniquely programmed to respond to a near field communications signal with data that uniquely identifies at least one of the type of plant, the plant ID, and geographic location where the plant will be located when mature, the NFC tag data being derived by a hash function using the plant ID number and the GPS coordinates of the location where the plant will be located when mature.

4. The system of claim 1 wherein the plant guide number further comprises one of the group of:

tag number 1, representing water level low and light level high;

tag number 2, representing water level high, and light level high;

tag number 3, representing water level medium, and light level high;

tag number 4, representing water level low, and light level medium;

tag number 5, representing water level high, and light level medium;

tag number 6, representing water level medium, and light level medium;

tag number 7, representing water level low, and light level low;

tag number 8, representing water level high, and light level low: and, tag number 9, representing water level medium, and light level low.

5. The system of claim 4 wherein the instructions further comprise generating a winterize schedule comprising:

locating a geographical coordinate set for a location of the first plant;

identifying a first 32° F. date for the location;

identifying a last 32° F. date for the location; and, calculating at least one of a winterize alert date and a fertilize alert date based on at least one of the first 32° F. date and the last 32° F. date.

6. The system of claim 4 wherein the hand held device is programmed to:

identify a code number related to the first plant ID from a durable plant tag;

send the code number to the server;

and the instructions further comprise:

deriving the first plant ID from the code number.

7. The system of claim 1, wherein the QR code is updated to reflect current climate conditions and the QR code capable of being resolved by an application to a website on a server.

8. The system of claim 1, wherein the second set of instructions stored in the second memory, which when executed by the second processor cause the server to:

generate a prune schedule for the first plant associated with the first plant ID;

iteratively advance through the prune schedule to locate a prune action date;

generate a prune alert; and send the prune alert to the hand held device.

9. The system of claim 1, wherein the horticultural characteristics of the first plant type include the scientific name of the plant including at least one of the kingdom, subkingdom, superdivision, division, class, subclass, order, family, genus, species, subspecies, and variety of the first plant type.

\* \* \* \* \*

UNITED STATES PATENT AND TRADEMARK OFFICE
CERTIFICATE OF CORRECTION

| | | |
|---|---|---|
| PATENT NO. | : 11,533,855 B2 | Page 1 of 1 |
| APPLICATION NO. | : 15/230015 | |
| DATED | : December 27, 2022 | |
| INVENTOR(S) | : Jack Davis et al. | |

It is certified that error appears in the above-identified patent and that said Letters Patent is hereby corrected as shown below:

In the Claims

<u>Claim 1, Column 20, Line 26</u>: change "a quick response (OR) code" to --a quick response (QR) code--;

<u>Claim 1, Column 20, Line 48</u>: change "(OR) code" to --(QR) code--;

<u>Claim 1, Column 20, Line 54</u>: change "read the (OR) code" to --read the (QR) code--;

<u>Claim 1, Column 20, Line 57</u>: change "send the (OR) code" to --send the (QR) code--; and <u>Claim 1, Column 20, Line 65</u>: change "receive the (OR) code" to --receive the (QR) code--.

Signed and Sealed this
Thirty-first Day of January, 2023

Katherine Kelly Vidal
*Director of the United States Patent and Trademark Office*